United States Patent [19]
Lai

[11] Patent Number: 5,960,056
[45] Date of Patent: Sep. 28, 1999

[54] METHOD AND APPARATUS FOR RECONSTRUCTING VOLUMETRIC IMAGES IN A HELICAL SCANNING COMPUTED TOMOGRAPHY SYSTEM WITH MULTIPLE ROWS OF DETECTORS

[75] Inventor: Ching-Ming Lai, Wakefield, Mass.

[73] Assignee: Analogic Corporation, Peabody, Mass.

[21] Appl. No.: 09/038,320

[22] Filed: Mar. 11, 1998

Related U.S. Application Data

[60] Provisional application No. 60/051,409, Jul. 1, 1997.
[51] Int. Cl.$^6$ ........................................................ A61B 6/03
[52] U.S. Cl. ................................. 378/4; 378/15; 378/901
[58] Field of Search .................................. 378/4, 15, 901

[56] References Cited

U.S. PATENT DOCUMENTS

| | | | |
|---|---|---|---|
| 5,291,402 | 3/1994 | Pfoh | 364/413.14 |
| 5,377,250 | 12/1994 | Hu | 378/15 |
| 5,430,785 | 7/1995 | Pfoh et al. | 378/19 |
| 5,457,321 | 10/1995 | Ichihara et al. | 250/363.04 |
| 5,740,224 | 4/1998 | Muller et al. | 378/11 |
| 5,796,803 | 8/1998 | Flohr et al. | 378/15 |
| 5,825,842 | 10/1998 | Taguchi | 378/15 |

FOREIGN PATENT DOCUMENTS 4224949 1/1993 Germany .

OTHER PUBLICATIONS

PCT International Search Report of PCT/US98/13533.

L.A. Feldkamp, L.C. Davis, and J.W. Kress, "Practical Cone-beam Algorithm," J. Opt. Soc. Am. A, vol. 1, p. 612, No. 6, Jun. 1984.

D.L. Parker, "Optimal Short Scan Convolution Reconstruction for Fan beam CT," Med. Phys., vol. 9, No. 2, p. 254, Mar./Apr. 1982.

*Primary Examiner*—David Vernon Bruce
*Attorney, Agent, or Firm*—Lappin & Kusmer

[57] ABSTRACT

In an improved method and apparatus for cone-beam reconstruction, a helical cone-beam system is provided, operable in a half-scan configuration, offering volumetric imaging results superior to conventional scanning techniques at double the pitch. The projection data of successive rotation angles are sorted into reordered parallel projections having different spatial positions with respect to the rotating axis. The reordered projections are interpolated to generate interpolated projections having a common spatial position along the rotation axis. The interpolated projections are convolved and backprojected to provide a volumetric image of the object. The invention is applicable to a range of computed tomography applications, including medical scanning, baggage scanning, and industrial product scanning applications.

68 Claims, 16 Drawing Sheets

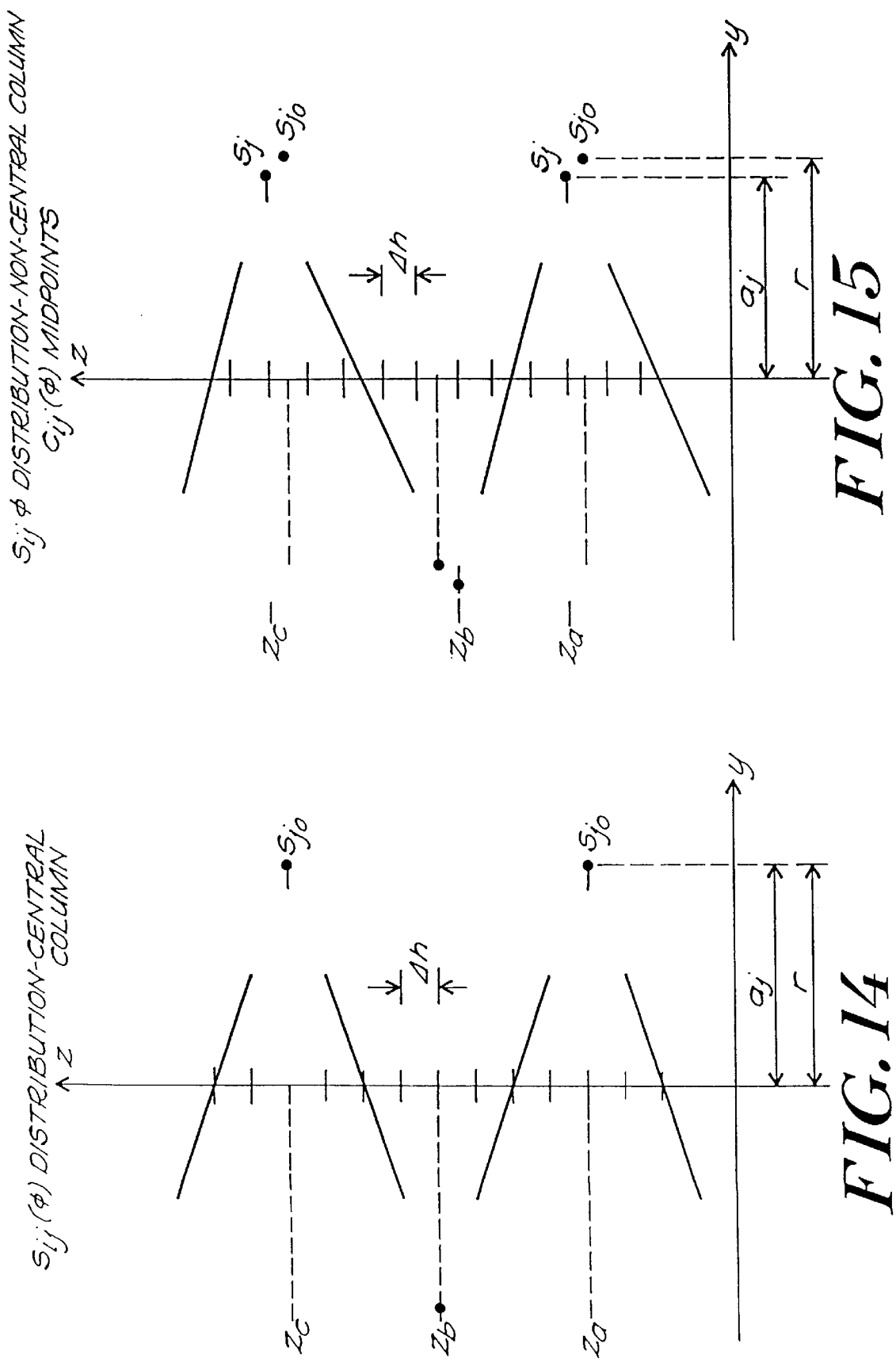

METHOD AND APPARATUS FOR RECONSTRUCTING VOLUMETRIC IMAGES IN A HELICAL SCANNING COMPUTED TOMOGRAPHY SYSTEM WITH MULTIPLE ROWS OF DETECTORS

RELATED APPLICATION

This application claims the benefit of U.S. Provisional Application No. 60/051,409, filed Jul. 1, 1997, the contents of which are incorporated herein by reference.

BACKGROUND OF THE INVENTION

In modern computed tomography (CT) scanner systems, an X-ray source generates an X-ray beam which interrogates an object and is incident on a sensor array. In third-generation CT systems, the source and sensor array are mounted on a gantry which rotates about the object. Successive sets of projections of the object are recorded at incremental gantry rotation angles. After completion of a half rotation of the gantry ("half-scan" system) or a full rotation ("full-scan" system), data from the successive rotation angles are combined in a process known as reconstruction to create a cross-sectional image of the object. In a stationary scan configuration, the object is fixed in position during each scan, while in a translational scan, or "helical" scan, the object translates relative to the gantry during a scan, improving system throughput.

In a conventional two-dimensional CT scanner, as shown in Prior Art FIG. 1, the X-ray beam 51 propagates in a planar fan shape 50 between a point source 54 and a sensor array 52 comprising a one-dimensional array of detector elements 53. The fan beam 50 is referred to as a "transaxial fan" because the plane of the fan is perpendicular to the rotation axis, i.e., the z-axis. A two-dimensional image reconstruction process collects the raw data at each rotation angle and following a half-scan, or full-scan, converts the data into a planar pixel image of the portion of the object 55 through which the x-rays have passed. Following each scan, the object may be translated along the z-axis to generate adjacent planar cross-sectional images or "slices" of the object 55 which can be combined to produce a volumetric image.

In a three-dimensional CT scanner, as shown in Prior Art FIG. 2, a conical X-ray beam 61, also referred to as a "cone beam", generated at a point source 54, projects through an object 55 and is incident on a two-dimensional sensor array 63. The array 63 comprises multiple rows 56 (rows 1 ... M) and multiple columns 62 (columns 1 ... N) of detectors which lie on a cylindrical surface 58. In this configuration, the X-ray cone beam 61 diverges not only along the xy-plane but also diverges along the z-axis.

Each cone beam 61 is composed of multiple layers of transaxial fan beams, three of which are indicated by the numerals 60A, 60B, 60C, each transaxial beam defined between the x-ray point source 54 and one of the rows 1 ... M of detector elements 56A, 56B, 56C. Note that with the exception of transaxial fan beam 60B, which lies along the xy-plane, the remaining transaxial fan beams 60A, 60C are not perpendicular to the z-axis of rotation, and therefore are not "transaxial" in the strictest sense. Instead, each remaining fan beam 60A, 60C is tilted relative to the xy-plane by a small angle $\beta$, referred to as the "conical angle" as shown in Prior Art FIG. 3. Within this definition, transaxial fan beam 60B, projected along the xy-plane can be envisioned as a transaxial fan beam having a conical angle of 0°.

The x-ray point source 54 and respective columns 1 ... N of detector elements 62 also define "axial" fan beams, three of which are indicated by numerals 64A, 64B, 64C as illustrated in Prior Art FIG. 4. Each axial fan beam 64 lies on a plane parallel to the rotation axis. With the exception of the fan beam 64B of detector column $j_0$, which lies directly on the yz-plane and therefore projects through the z-axis at all rotation angles, the axial fans of the remaining columns 1 ... N diverge from the yz-plane by an "axial angle" of $\gamma$. The central axial fan beam 64B, projected along the yz-plane can be envisioned as an axial fan beam having an axial angle $\gamma$ of 0°. While in rotation, a set of line projections are provided at each of a plurality of successive rotation angles of the gantry. The angle of a line projection measured on the xy-plane is referred to as the view angle of the projection. Thus, at rotation angle $\theta$, the line projection within each axial fan beam at axial angle $\gamma$ is associated with the same view angle of $\phi = \theta + \gamma$.

In practice, a conventional two-dimensional reconstruction algorithm is insufficient for reconstructing a three-dimensional volumetric image from cone-beam data collected with a two-dimensional detector array. The three-dimensional cone-beam data cannot be accurately resolved into independent parallel layers along the z-axis for introduction into two-dimensional reconstruction since each transaxial fan beam lies at a conical angle $\beta$ to the z-axis, as described above. Performing two-dimensional reconstruction using this data would therefore result in reconstruction errors for each set of fan beam data, with the exception of the central fan beam 60B along the xy-plane. The reconstruction errors worsen as the conical angle $\beta$ increases. A more accurate three-dimensional reconstruction technique known as cone-beam reconstruction for stationary scan configurations is described in:

1. L. A. Feldkamp, L. C. Davis, and J. W. Kress, "Practical Cone-beam Algorithm", J. Opt. Soc. Am. A, Vol.1, p612, No.6, June 1984.

The foregoing discussion applies to scanning an object which is stationary with respect to the z-axis. In another form of scanning, known in the art as a helical scan, the object translates relative to the gantry along a translation axis, usually parallel to the z-axis, at a constant speed during gantry rotation. From the perspective of the object, the x-ray source and sensors can be envisioned as circling about the object in a helical trajectory during data collection. In a helical scan of a conventional system with single-row detectors, the projection data are first interpolated to the z position of each slice for generating its planar image. These planar images are located contiguously along the z-axis. The contiguous slices can be combined and further processed for various modes of three-dimensional display. Unfortunately, in a cone-beam system, the z-axis translation causes the collected data to deviate further from that data which is required for standard two-dimensional or three-dimensional reconstruction techniques. As a result, the reconstruction errors arising from a helical scan of a cone-beam system are worse than that of a stationary scan. Reconstruction and enhancement methods for cone-beam helical scans are described in:

2. U.S. Pat. No. 5,291,402 issued Mar. 1, 1994, to A. H. Pfoh, "Helical Scanning Computed Tomography Apparatus";

3. U.S. Pat. No. 5,377,250 issued Dec. 27, 1994, to H. Hu, "Reconstruction Method for Helical Scanning Computed Tomography Apparatus with Multi-row Detector Array";

4. U.S. Pat. No. 5,430,783 issued Jul. 4, 1995, to H. Hu, N. J. Pele, and A. H. Pfoh, "Reconstruction Method for Helical Scanning Computed Tomography Apparatus with Multi-row Detector Array Employing Overlapping Beams"; and 5. D. L. Parker, "Optimal Short Scan Convolution Reconstruction for Fan beam CT", Med. Phys., Vol.9, No.2, p254, March/April 1982.

In the foregoing references, data are collected over a full rotation of the gantry, i.e., "full-scan", to reconstruct the volumetric image over the scanned region. However, the image may be reconstructed based on data collected in half rotation of the gantry, i.e., "half-scan". Half-scan imaging offers the advantage of doubling the throughput rate or "pitch" compared to a full-scan, where "pitch" is the extent of object translation along the z-axis during a full rotation of the gantry. In a stationary cone-beam system, the full-scan reconstruction technique provides images generally superior to those of the half-scan reconstruction technique. This is due to the fact that in a full scan, the axial fan beams 66, 68 at view angles $\phi$ and $\phi+\pi$ respectively diverge in opposite directions as sketched in Prior Art FIG. 5A, which, when the data is reordered with data from other mutually-opposing views, tends to cancel some of the reconstruction errors. On the other hand, at each view angle $\phi$ of a half scan, there is no corresponding fan beam 68 at view angle $\phi+\pi$ which presents an opposite view of the same region of the object.

In a helical scan as shown in Prior Art FIG. 5B, the opposing axial fan beams 66, 68 at view angles $\phi$ and $\phi+\pi$ respectively do not correspond to the same z position. As a result, a helical full-scan contains larger reconstruction errors than a stationary full scan. In both full-scan and half-scan cone-beam systems, reconstruction errors increase with increased divergence of the axial X-ray beam. If additional detector rows 56 are used, or if the width of each row increases, reconstruction errors become more severe as the result of increasing the conical angle $\beta$.

Past attempts at mitigation of reconstruction error have met with various results. The "algebraic reconstruction technique" (ART) has been employed as an alternative to two-dimensional filtered backprojection in exceptional cases, for example in situations where considerable artifacts are generated in backprojection due to extreme contrast in the object. The ART technique employs a trial-and-error method to reconstruct the image. At each view angle, the projections are generated from the reconstructed image and compared with the original collected projections. The differences are then weighted and backprojected to the image to reduce the discrepancy with the collected projections at that view angle. This trial-and-error method is applied on a view-by-view basis, and it is preferable to process in a non-sequential order of view angle, such that the successive view angles are as different, i.e., as orthogonal, as possible. Convolution is not used, and results are often data-dependent. Convergence is usually slow and unpredictable.

In the well-known reconstruction technique referred to in the art as "bone correction", the image is analyzed to distinguish bone from soft tissues, and projections are regenerated from only the bone regions of the reconstructed image to estimate the error in the collected projections due to X-ray beam hardening by the bone. The estimated errors are then used to reconstruct an image for correcting the original image. This technique requires image-specific processing to generate projections from only the isolated sections of the image and is therefore not applicable to general reconstruction error mitigation.

SUMMARY OF THE INVENTION

The present invention is directed to an improved method and apparatus for cone-beam reconstruction which overcomes the limitations of the prior art. A helical cone-beam system is provided, operable in a half-scan configuration, offering volumetric imaging results superior to prior art full scan techniques at double the pitch.

The present invention comprises a method of reconstructing a volumetric image in a computed tomography system. In a preferred embodiment, conical X-ray beams are projected from an X-ray source toward a two-dimensional detector array. The X-ray source and the detector array are mounted on a gantry and rotate about a rotation axis to interrogate the object at successive rotation angles during the scan. The detector array is arranged in columns along the rotation axis, and in rows along a tangential direction centered about the X-ray source. The rotation axis is referred to herein as the z-axis, and the xy-plane as the plane normal to the rotation axis.

During a scan, the object is simultaneously and continuously translated along a translation axis substantially parallel to the rotation axis. At each rotation, or cone beam projection, angle, the beam intensity is sensed by each element of the detector array, each element defining a projection path (i.e. line projection) with the X-ray source. The angle of the projection paths as measured on the xy-plane is the view angle of the projection. The projection paths of successive rotation angles are sorted or interpolated into reordered projections of the same view angle. The projections reordered from the detectors with the same conical angle are parallel to each other, but slightly tilted away from the xy-plane by a small angle equal to the conical angle.

Due to continuous translation of the object, the reordered projections have different spatial positions with respect to the z-axis. Each row of the reordered projections is interpolated to generate interpolated projections having the same spatial positions along the z-axis at each view angle. The interpolated projections are convolved and backprojected to generate a volumetric image of the object.

In a preferred embodiment, the tangential direction centered about the X-ray source is substantially perpendicular to the rotation axis and lies on the xy-plane. The system preferably operates in a half-scan mode.

The step of interpolating the reordered projections preferably comprises determining a midpoint of each projection path between the X-ray source and corresponding detector element to represent the spatial position of the projection path with respect to the rotation axis. The midpoints of line projections of the same detector column preferably lie along a line parallel to the translation axis. The midpoints of projections of detectors of the same row lie on a curve slightly deviated from the circular arc.

A potential artifact that may result from the step of interpolating the reordered projections can be avoided by using an offset function, for example, a periodic triangular function, to offset the z position of the reordered projections as a function of the view angle. The precision of the interpolation, and hence the image resolution along the z-axis, can be enhanced by using higher-order interpolation and by doubling the number of interpolating points.

A separation line is calculated as the line defined between respective positions of the source at opposite view angles. The separation line serves to separate the projections of axial fans at opposite view angles for determining which projections contribute to the backprojection.

The step of backprojecting can be made more efficient by making the step of backprojection along the xy-plane as the most iterative set of computations followed by backprojection along the rotation axis as the less iterative set of computations.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Prior Art

Prior Art

Prior Art

Prior Art

Prior Art

Prior Art

FIG. 14 illustrates the distribution of constant-z interpolated projections $S_{ij}(\phi)$ for the central detector column in accordance with the present invention.

FIG. 15 illustrates the distribution of constant-z interpolated projections $S_{ij}(\phi)$ for a detector column located a distance from the central column, using $c_{ij}$ as the midpoint for purposes of the interpolation, in accordance with the present invention.

DETAILED DESCRIPTION OF THE PREFERRED EMBODIMENTS

I. Overview

It is well known that in a conventional stationary, single-row detector, half-scan computed tomography system, the transaxial fan beam data required for accurate reconstruction lies within the half-scan rotation angle of $\pi$ plus an additional angle of $2\gamma_{max}$, which is the angular span of the fan beam, as described in Parker, cited above. Without the extra $2\gamma_{max}$ angle, some of the projections are absent and some are redundant (double-sampled) near the starting rotation angle $\theta$ or the finishing rotation angle $\theta+\pi$. The extra $2\gamma_{max}$ scan angle ensures that no projection is absent for reconstruction near the starting and finishing angle. For these double-sampled data, each projection on the left side of the fan at the starting angle $\theta$ is paired with a parallel projection at the right side of the fan at the opposite angle $\theta+\pi$, in which they project along the same path through the object but in opposite directions. The redundancy is compensated by applying proper weighting to average the opposed projections, such that all data are utilized and any discontinuity between the starting and finishing angles is minimized.

This phenomenon is much more complicated for helical scans of a cone-beam system with multiple rows of detectors, where each redundant projection in a pair is collected from a detector in a different row. Although the projections are parallel in xy space, in which the z dimension is disregarded, they have different angles relative to the z-axis because different rows of detectors have different conical angles $\beta$. For this reason, the compensation technique of weighting the redundant projections in a cone-beam system is less effective than in a conventional system with a single row of detectors. Furthermore, unlike a stationary full-scan where the divergence of the X-ray with respect to the scanned object is symmetrical between the first and second half rotations, the cone-beam helical half-scan lacks such symmetry.

The present invention addresses the need for an improved cone-beam reconstruction technique for data collected in a helical half-scan. The novel technique avoids the ill effect of the fan-beam reconstruction algorithm and generates a more accurate three-dimensional image. It also reduces the amount of computations by using parallel-beam backprojection in xy space.

Figure 1:
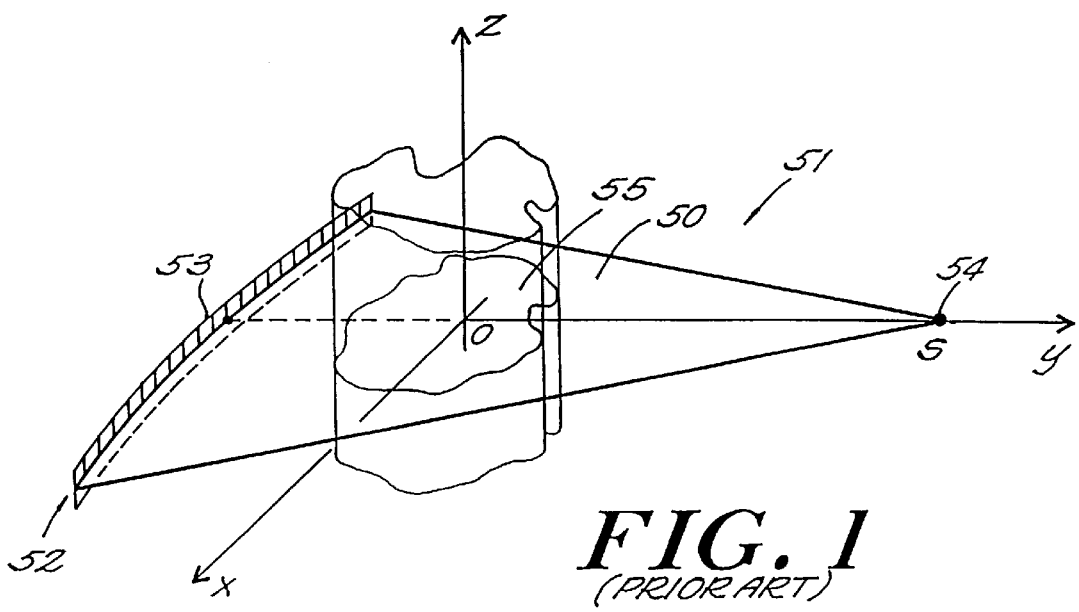
FIG. 1 illustrates an X-ray source and a single row of detectors defining a transaxial fan beam perpendicular to the z-axis of rotation in a prior art conventional computed tomography system.
Figure 2:
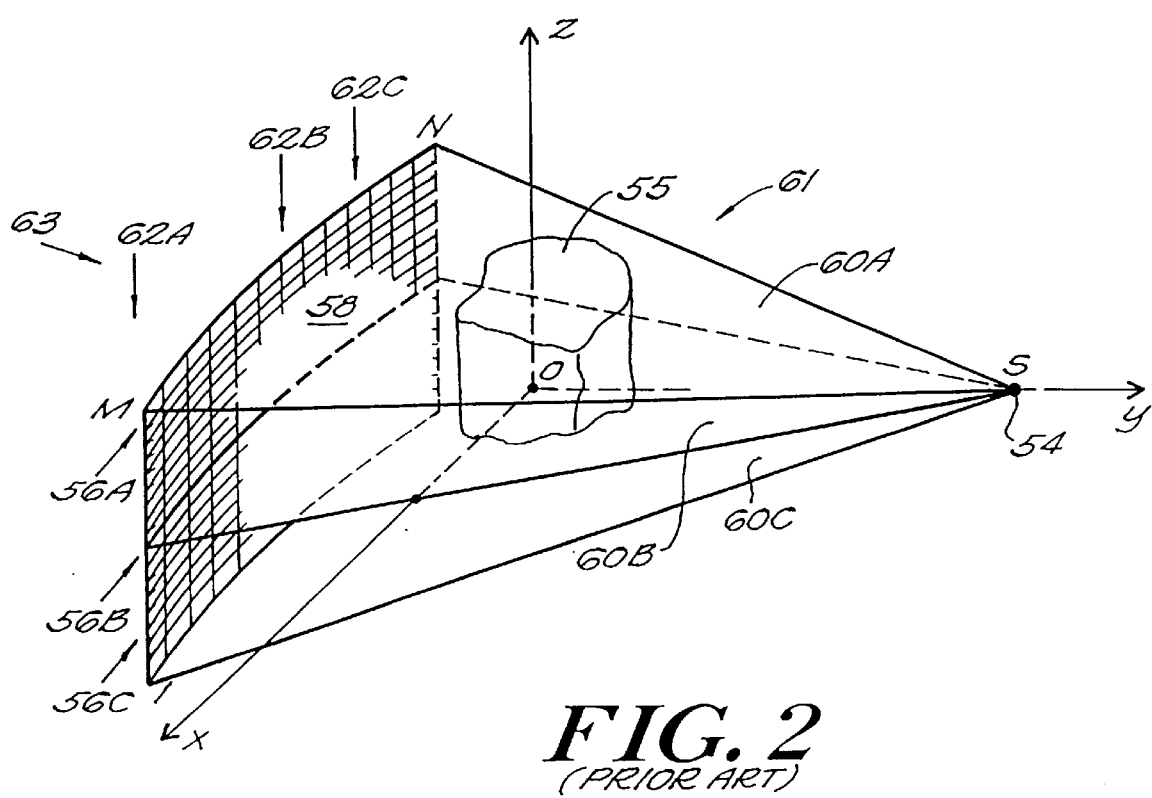
FIG. 2 illustrates an X-ray source and a multiple-row detector array defining multiple transaxial fan beams and multiple axial fan beams in a prior-art cone-beam tomography system.
Figure 3:
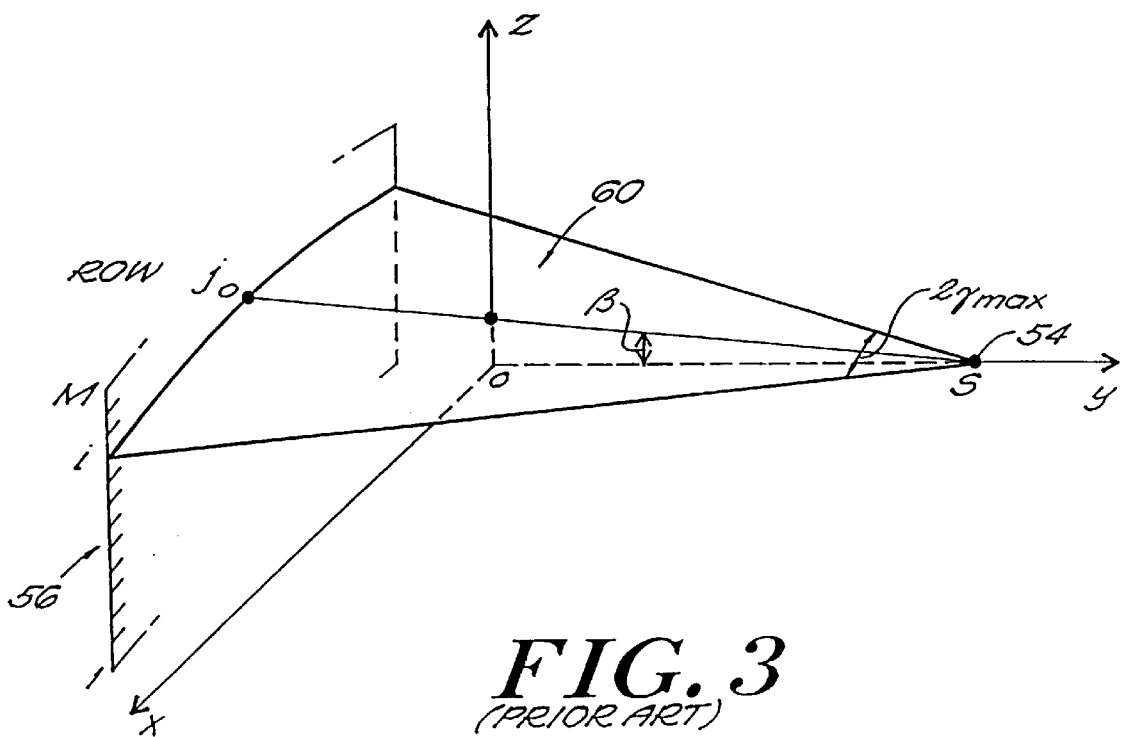
FIG. 3 illustrates the transaxial fan beams of the system of FIG. 2, each directed to a different row of detectors and having a transaxial fan angle of $2\gamma_{max}$ and lying at a conical angle of $\beta$ relative to the xy-plane.
Figure 4:
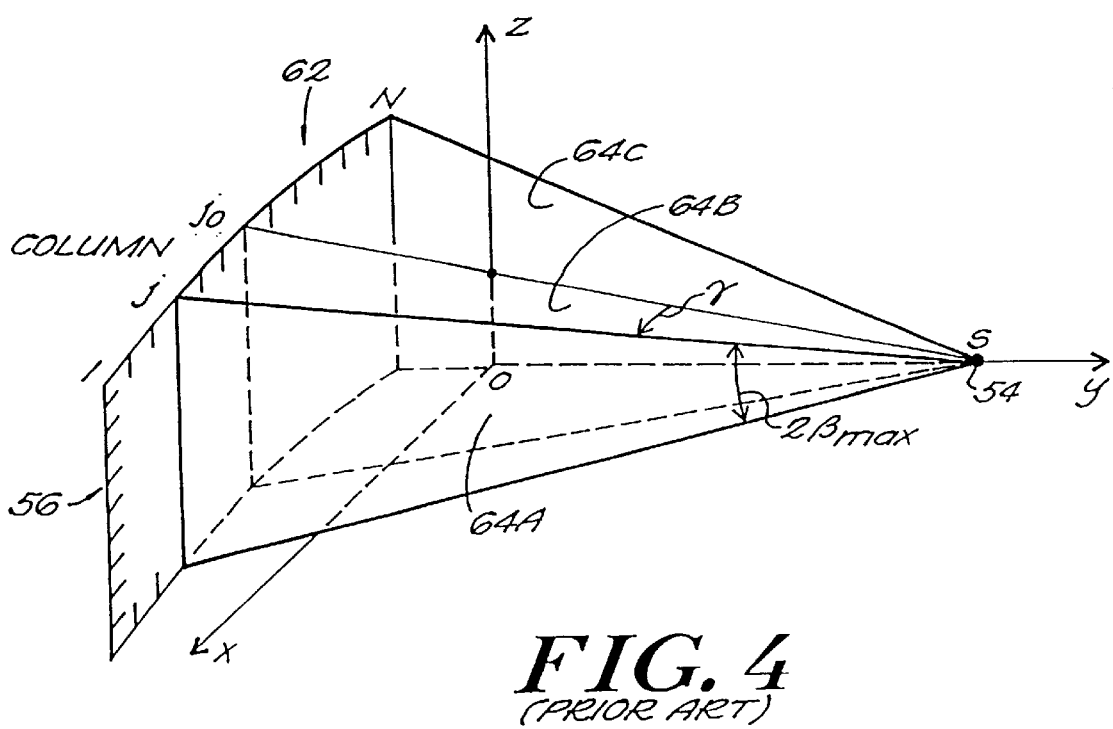
FIG. 4 illustrates the axial fan beams of the system of FIG. 2, each directed to a different column of detectors and having an axial fan angle of $2\beta_{max}$ and lying at an angle of $\gamma$ relative to the yz-plane.
Figure 5A:
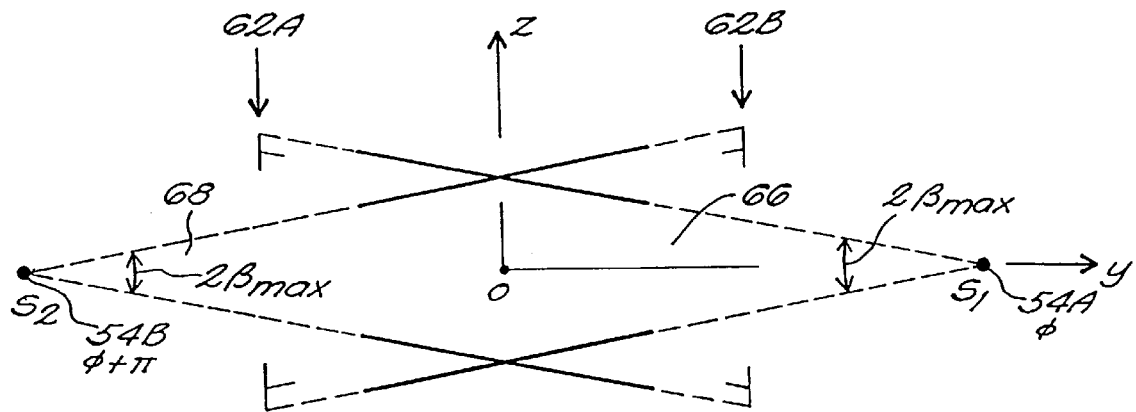
FIG. 5A depicts opposed axial fan beams at view angles $\phi$ and $\phi+\pi$ in a stationary scan.
Figure 5B:
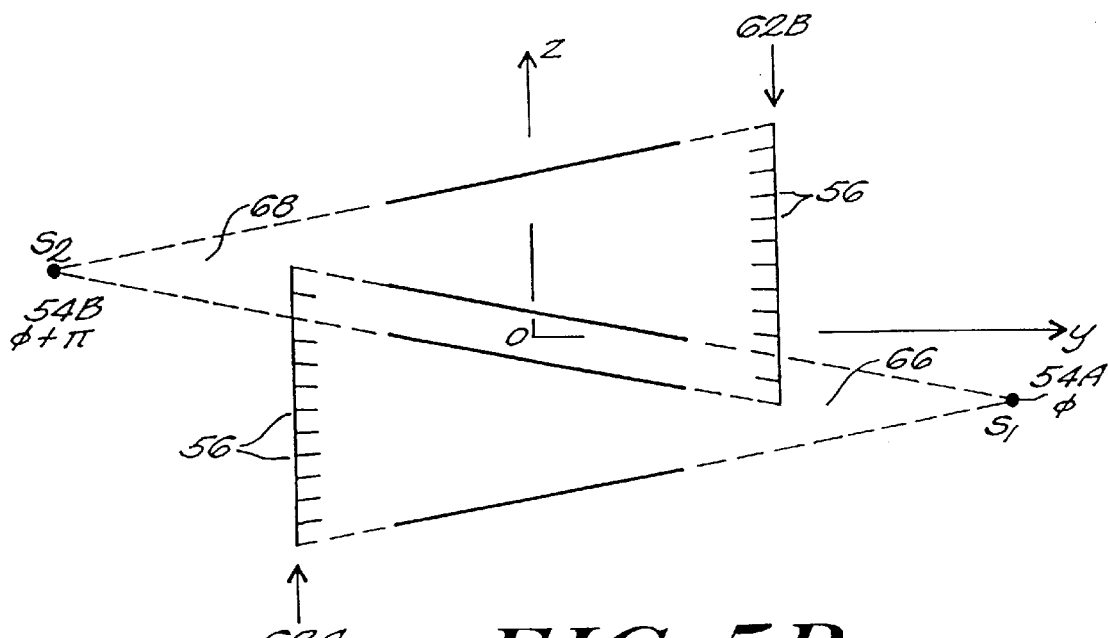
FIG. 5B depicts opposed axial fan beams at view angles $\phi$ and $\phi+\pi$ in a helical scan.
Figure 6:
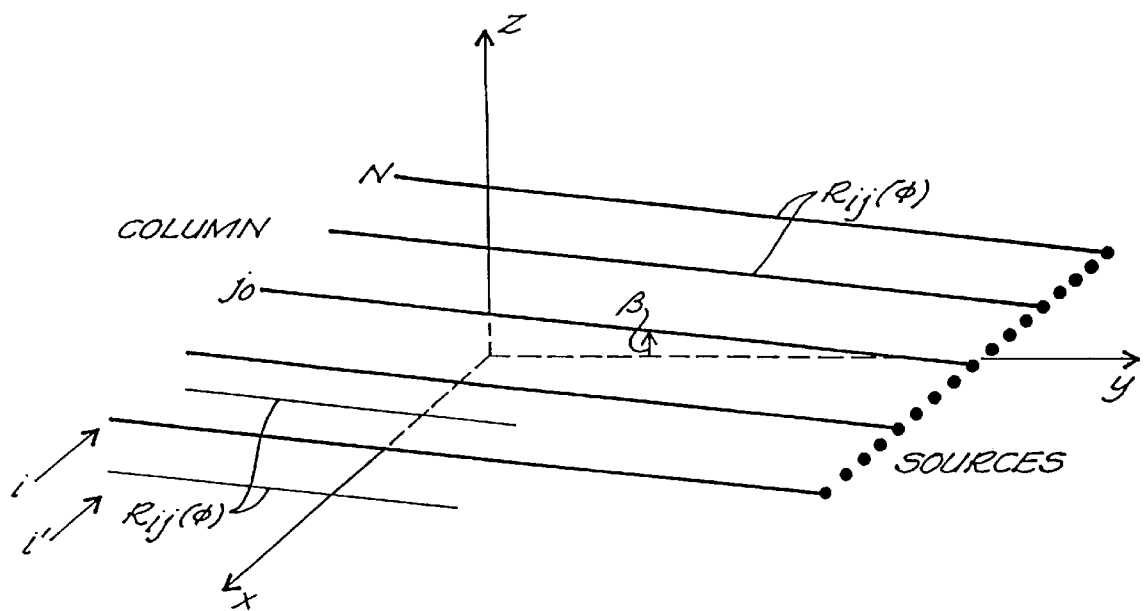
FIG. 6 is an illustration of parallel projections reordered from transaxial fan beam projections, in accordance with the present invention.

In the improved technique of the present invention, the collected data are first converted into projections as a function of the logarithm of the signal intensity sensed at each detector, followed by application of certain corrections for offset, nonlinearity, and other corrections in accordance with well-known computed-tomography techniques. From nearby rotation angles, the fan-beam projections (for each detector row) are reordered into parallel-beam projections $R_{ij}(\phi)$ as illustrated in FIG. 6. At each parallel-beam view angle $\phi$, the reordered projections are parallel to each other in xy space. However, because the projections $R_{ij}(\phi)$ are reordered from different fan-beam rotation angles, the parallel-beam projections within a view angle $\phi$ are at different z positions with respect to the object which translates in the direction of the z-axis, or translation axis. The present invention compensates for this by interpolating projections derived from the same detector column or channel, but different rows of the detector array, to constant-z positions in a process referred to herein as "constant-z interpolation".

The constant-z interpolated parallel-beam projections are sampled at equal angular intervals for each row. To prepare for filtered backprojection, projections from each detector row are interpolated into equal spatial intervals. The equally-spaced projections are then filtered by a convolution kernel for each detector row in a manner similar to the convolution for reconstructing a two-dimensional image from parallel-beam projections.

In the final stage of reconstruction, the convolved parallel-beam projections are backprojected using three-dimensional backprojection techniques. In the preferred configuration, for each value of $\phi$, all rows of projections at parallel-beam view angles $\phi$ and $\phi+\pi$ are grouped together to backproject for those voxels scanned. Each voxel is backprojected from the convolved projection which passes through the voxel either at view angle $\phi$ or $\phi+\pi$. Since the voxel is not precisely located at the path of a projection, the value for backprojection to a voxel is interpolated from adjacent projections.

In the description to follow, assume conical beams are emitted from a point source to a two-dimensional array of detectors. Assume also that the detector array lies on a cylindrical surface centered about an axis which passes through the source, and that the detector columns lie parallel to the rotation axis, or z-axis, and perpendicular to the xy-plane. The present invention is equally applicable to other conceivable helical scanning geometries, however, for purposes of the following illustration, the foregoing assumptions apply. Note that for purposes of the present invention, the term "channel" refers to a detector element in a given row of detectors, while the term "column" refers to an arrangement of a column of channels (or elements) in adjacent detector rows, i.e., parallel to the rotation axis.

II. Reordering of Projections From Fan to Parallel Beams

The initial step of reordering the fan beam projections collected from each row of detectors into parallel-beam projections independent of other rows will now be described in detail with reference to the various drawings. Assuming that $P_{ij}(\theta)$ represents the amplitude of a line projection derived from a detector located in the jth column and ith row at fan-beam rotation angle $\theta$, and $R_{ij}(\phi)$ represents the reordered projection amplitude in the jth column of ith row at parallel-beam view angle $\phi$, then $$R_{ij}(\phi)=P_{ij}(\phi-(j-j_o)*\delta) \tag{1}$$

where $\delta$ represents the angular spacing between adjacent columns and $j_o$ represents the central column. If the detector array has M rows with N columns or detector channels per row, then i=1,2, . . . , M
j=1,2, . . . , N $$j_o=(N+1)/2 \tag{2}$$

assuming the detector array 63 (see FIG. 7) is symmetrical about the rotation axis. Since the fan angle of the transaxial fan is $2\gamma_{max}$, the angular spacing $\delta$ is related to the fan angle by:

$$\delta=2\gamma_{max}/(N-1). \tag{3}$$

During a scan, the gantry rotates about the z-axis and the data are collected at successive intervals of the gantry rotation angle:

$$\theta=\theta_k=k*\Delta\theta \tag{4}$$

where k is an integer and $\Delta\theta$ is the increment of the gantry rotation angle between successive fan beam projections.

Assuming that the parallel-beam view angle $\phi$ is chosen to have the same rotation angle increment $\Delta\theta$, as preferred, then $\phi=\phi_m=m*\Delta\theta$, with integer m=0, 1, 2, . . . If the data are acquired at such a rate that the incremental rotation angle is equivalent to the angular spacing between columns, or $\Delta\theta=\delta$, then Equation 1 becomes $$R_{ij}(\phi)=P_{ij}((m+j_o-j)*\Delta\theta)=P_{ij}(\theta_k) \text{ with } k=m+j_o-j \tag{5}$$

In Equation 5, because $(m+j_o-j)$ is an integer, the reordered projection $R_{ij}(\phi)$ can be obtained from $P_{ij}(\theta_k)$ at successive fan-beam rotation angles.

In the case where the incremental rotation angle between successive fan beam projections is greater than the angular column spacing, i.e., $\Delta\theta>\delta$, or $\Delta\theta>a*\delta$, with a>1. Equation 1 becomes $$R_{ij}(\phi)=P_{ij}((m+(j_o-j)/a)*\Delta\theta)=P_{ij}(\theta_{ka}), k_a=m+(j_o-j)/a \tag{6}$$

In this case, $k_a$ is not an integer unless $(j_o-j)$ is divisible by a.

Let $k \leq k_a < k+1$, where k is the truncated integer of $k_a$ with a remainder of $f=k_a-k$. This gives $$\theta_{ka}=\theta_k+f*\Delta\theta \text{ with } 0 \leq f<1 \tag{7}$$

Combining Equations 6 and 7, the reordered projections $R_{ij}(\phi)$ can be calculated as $$R_{ij}(\phi)=(1.0-f)*P_{ij}(\theta_k)+f*P_{ij}(\theta_{k+1}) \tag{8}$$

if linear interpolation is used. Therefore, Equation 8 applies to the derivation of reordered projections $R_{ij}(\phi)$ in a system where the incremental rotation angle is greater than the angular column spacing, or $\Delta\theta>\delta$, while Equation 5 applies where they are equal, $\Delta\theta=\delta$.

III. Constant-z Interpolation

The resulting reordered projections $R_{ij}(\phi)$ illustrated in FIG. 6 for all channels j at a view angle $\phi$ are parallel to each other because they are derived from detectors of the same row i. However, they are not parallel to reordered projections $R_{i'j}(\phi)$ from other rows i', because of the difference in conic angle between rows i and i'. Moreover, the location of each reordered projection along the z-axis is column-dependent because, in a helical scan, each projection is reordered from a fan beam of the same detector at a different z position. Accurate convolution, later performed as a precursor to the backprojection process, requires that the reordered projections lie on or nearly on the plane of the slice selected for convolution. For this reason, the reordered projections $R_{ij}(\phi)$ of row i, parallel in the xy space, but considerably separated in z-position, are interpolated or, in other words, re-sampled, to a set of projections still parallel in xy space but at the constant z-position of the reconstructing slice.

In the next step of the present invention, in a process referred to as constant-z interpolation, the reordered projections $R_{ij}(\phi)$ within the same column are used to generate projections at a constant z-position, and therefore suitable for convolution. Following constant-z interpolation, the interpolated reordered projections of all columns, even though they are not exactly perpendicular to the z-axis (i.e., their cone angles vary), are made to closely correspond to a constant z-position for each interpolated row i at each view angle $\phi$.

With the exception of the projection path corresponding to the central row of detectors $i_0$, no projection paths are exactly perpendicular to the z-axis. Therefore, the z-coordinate of each projection varies along its path between the source and detector element. A reference point referred to as the "midpoint" of the projection path is selected to represent the z-position of the projection. The "midpoint" is defined as the point of intersection between the projection path and a plane passing the z-axis and normal to the projection path (or, more precisely, a plane passing through the z-axis and normal to the axial fan containing the projection). Note that the midpoint of a projection line is not necessarily halfway between the source and detectors, nor does it necessarily correspond with the rotation axis. The z-coordinate of the midpoint defines the z-position of the projection path. The midpoints of projections of the same axial fan, i.e, the same column, lie along a line parallel to the z-axis, while midpoints of projections derived from the same transaxial fan, i.e., the same row, lie on a curve slightly deviated from a circular arc.

Figure 7:
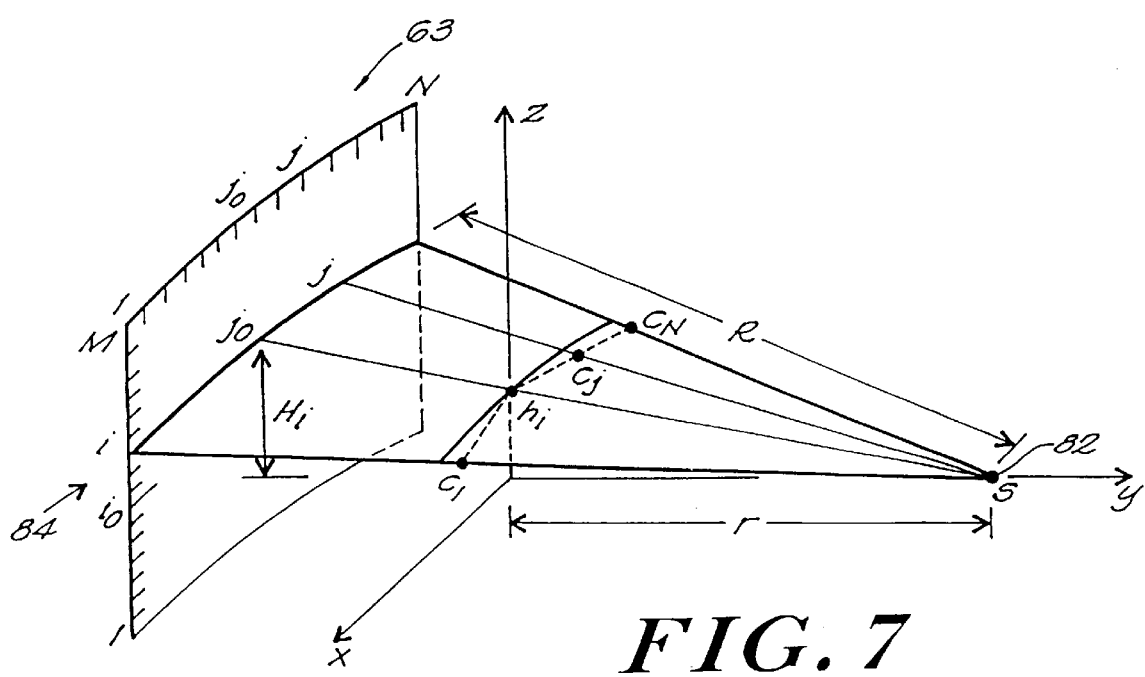
FIG. 7 is an illustration of the geometry of a transaxial fan beam and the midpoints of corresponding projection paths in accordance with the present invention.
Figure 8:
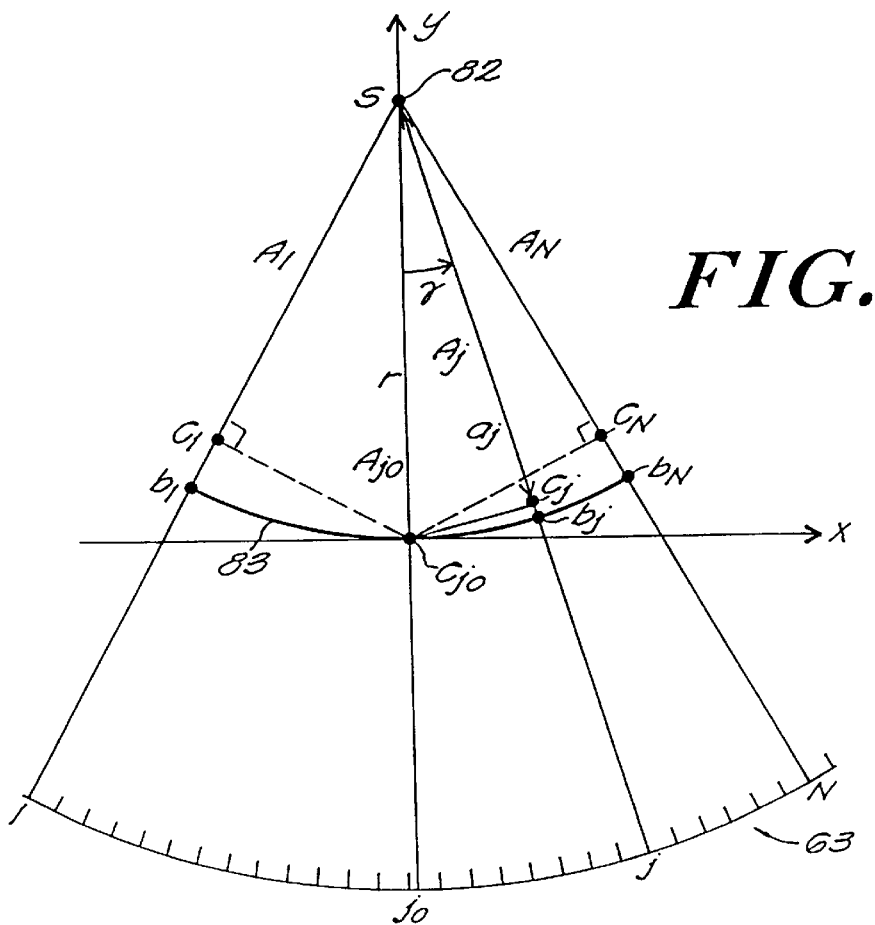
FIG. 8 is a top view of the illustration of midpoints of the projection paths of FIG. 7 in accordance with the present invention.

The loci of the midpoints on a transaxial fan are shown in FIG. 7, and marked as $c_1 \ldots c_N$ corresponding to detector channels $1 \ldots N$ in detector row 84. A top view of the midpoints $c_1 \ldots c_N$ is illustrated in FIG. 8, where a projection path such as $A_j$ is derived from the central row of detectors of the axial fan perpendicular to the xy plane. Using detector column j as an example, $c_j$ is the midpoint of the projection path $A_j$, and $b_j$ lies on the circular arc 83 which is centered about the X-ray source and passing the z-axis. For the projection $A_{j_o}$ of the central detector column $j_o$, midpoint $c_{j_o}$ intersects the circular arc 83 and coincides with the center of rotation O. For other detector channels, the distance $a_j$ from the X-ray source 82 to the midpoint $c_j$ is slightly shorter than the radius r of the circular arc 83. The distance $a_j$ can be represented as:

$$a_j = r^*\cos(\gamma) = r^*\cos((j-j_o)^*\delta) \tag{9}$$

where $j_o$ is central detector column number, and $\delta$ represents the angular spacing, as defined earlier.

Figure 9:
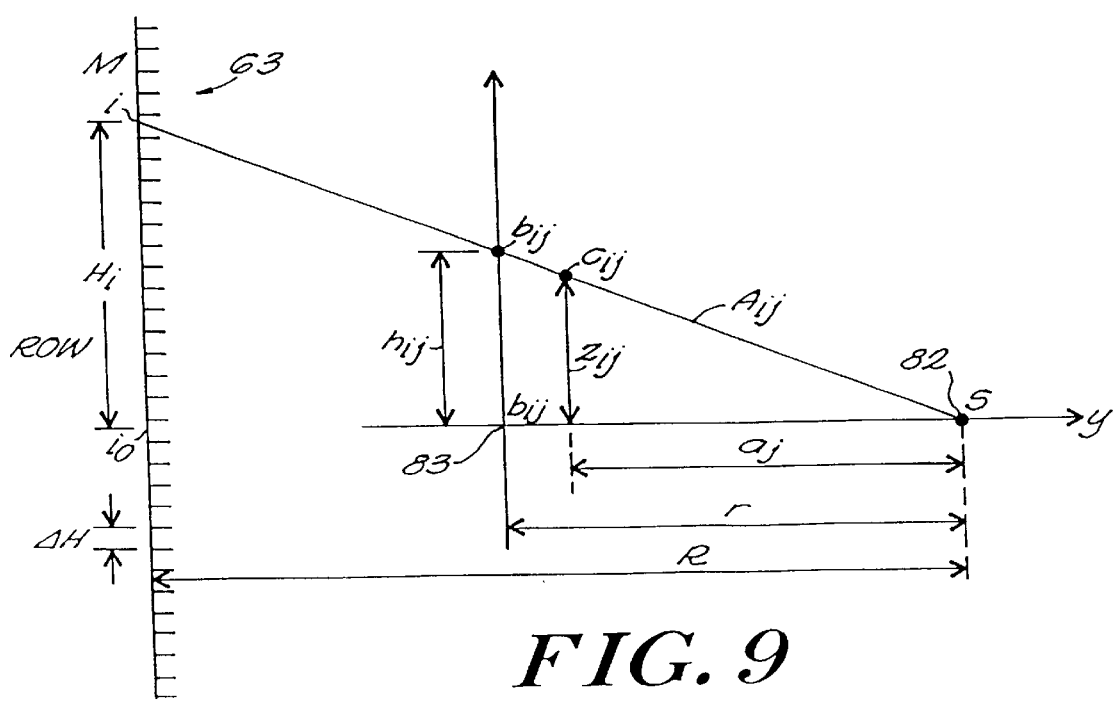
FIG. 9 is a side view of the illustration of the loci of midpoints of the projection paths of FIG. 7 in accordance with the present invention.

The loci of midpoints from the jth axial fan are illustrated in FIG. 9 on the yz plane. The midpoint $c_{ij}$ of a projection path $A_{ij}$ and its corresponding z-coordinate $z_{ij}$ are shown, with the index i indicating the projection of the ith detector row of rows $1 \ldots M$. The point corresponding to $b_j$ of FIG. 8 is denoted as $b_{ij}$, and its z-coordinate is $h_{ij}$. Assuming a cylindrical detector array 63 centered about the X-ray source, the radial distance of the detector array 63 and the radial distance of the center of rotation O from the X-ray source are referred to as R and r respectively. Assuming the z-axis position of the ith detector row is $H_i$, then the z-coordinate of point $b_{ij}$ in FIG. 9 can be calculated as $$h_{ij} = H_i{}^*r/R = h_i \tag{10}$$

which is the same for all detector channels within the same row; therefore the index j can be omitted. If the spatial interval between adjacent detector rows is represented by $\Delta H$, then the z-coordinate increment of $h_{ij}$ between successive rows is:

$$\Delta h = \Delta H^*r/R. \tag{11}$$

The z-coordinate $h_{ij}$ of point $b_{ij}$ can therefore be expressed as $$h_{ij} = h_i = (i-i_o)^*\Delta h \tag{12}$$

where $i_o$ is the central row number.

From the geometry of FIG. 9, the z-coordinate $z_{ij}$ of the midpoint $c_{ij}$ can be calculated as a proportion of the distance $a_j$ to the radius r, relative to $h_{ij}$:

$$z_{ij} = h_{ij}{}^*a_j/r. \tag{13}$$

Assuming that the object translates for a distance D during a gantry rotation angle of $\pi$, equivalent to a pitch of 2D for a helical scan, the z-position of the fan beam projection $P_{ij}(\theta)$ is:

$$z_{ij}(\theta) = z_{ij} + \theta^*D/\pi, \tag{14}$$

where $\theta$ represents the rotation angle.

Combining Equations 12 through 14:

$$z_{ij}(\theta) = (i-i_o)^*\Delta h^*a_j/r + \theta^*D/\pi \tag{15}$$

Using the relation $\theta = \phi - (j-j_o)^*\delta$ in Equation 1, the z-position $z_{ij}(\phi)$ for the reordered parallel-beam projection $R_{ij}(\phi)$ can be written as:

$$z_{ij}(\phi) = (i-i_o)^*\Delta h^*a_j/r + (\phi - (j-j_o)^*\delta)^*D/\pi \tag{16}$$

With the z-position given in the above Equation 16 for each projection path, the reordered projections $R_{ij}(\phi)$ can be interpolated from adjacent rows along the z-direction, such that the interpolated projections $S_{ij}(\phi)$ have a constant z-position for each row. Assume the constant z-position is chosen to be equal to the z-position of the central column $j_o$:

$$z_{ij_o}(\phi) = (i-i_o)^*\Delta h + \phi^*D/\pi, \tag{17}$$

where, for the central column $j_o$, $a_j = a_{j_o} = r$ and $j = j_o$.

If i' is the corresponding row number in column j with this z-position, then combining Equations 16 and 17:

$$(i'-i_o)^*\Delta h^*a_j/r + (\phi - (j-j_o)^*\delta)^*D/\pi = (i-i_o)^*\Delta h + \phi^*D/\pi$$

or, $$i' = i + (j-j_o)^*\delta^*D^*r/(\Delta h^*a_j{}^*\pi). \tag{18}$$

with $a_j$ given by Equation 9. Note that Equation 18 is independent of the parallel-beam angle $\phi$, and therefore the projections will be interpolated in exactly the same manner for every view angle.

In general, i' is not an integer. Let k be the truncated integer of i', that is $$i'=k+f_k \tag{19}$$

with $0 \leq f_k < 1.0$. If linear interpolation is employed, the constants interpolated projections $S_{ij}(\phi)$ can be calculated from two adjacent rows k and k+1 of the reordered projections as $$S_{ij}(\phi)=(1.0-f_k)*R_{kj}(\phi) +f_k*R_{k+1,j}(\phi) \tag{20}$$

Higher-order interpolation methods are preferred to calculate for $S_{ij}(\phi)$, to obtain more accurate results.

Figure 10A:
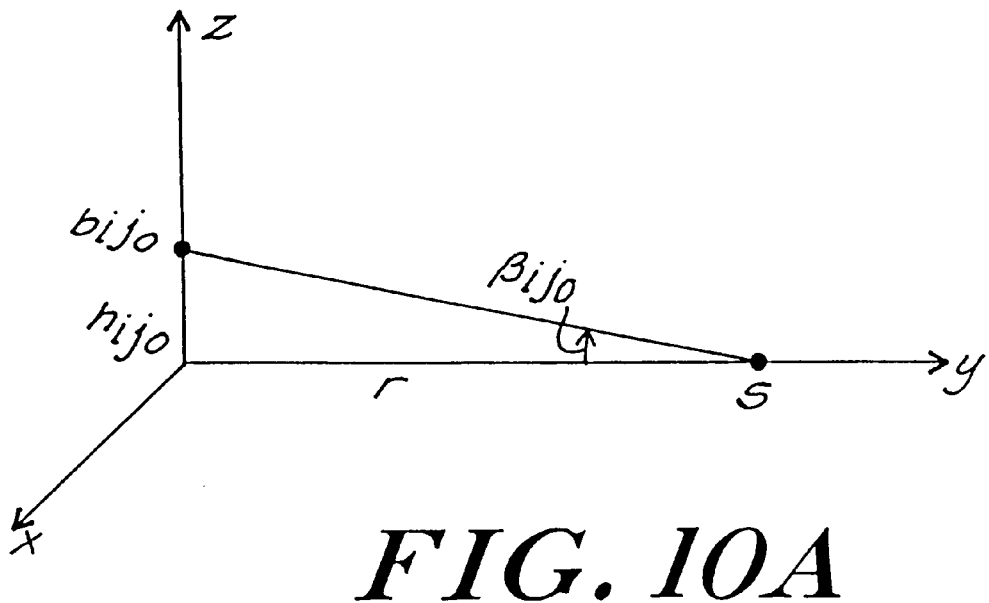
FIG. 10A is an illustration of the conical angle of the central detector column $j_0$ in accordance with the present invention.
Figure 10B:
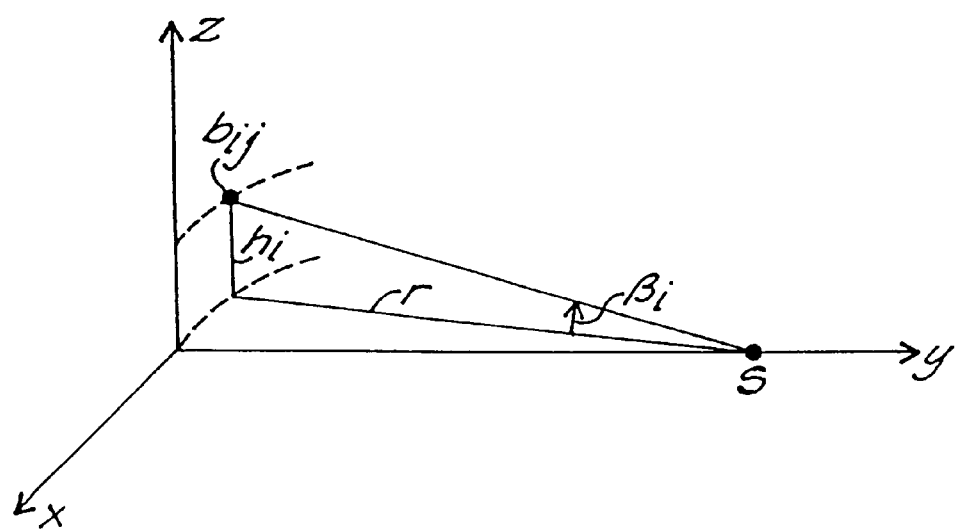
FIG. 10B is an illustration of the conical angle of the jth column of detectors in accordance with the present invention.

Although each row of constant-z interpolated projections $S_{ij}(\phi)$ represents parallel-beam projections in xy space at a constant-z position, they are not truly parallel in three-dimensional space as each projection has a different conical angle $\beta$, referring to the angle $\beta$ between the projection path and the xy-plane. The conical angle for each projection $S_{ij}(\phi)$ can be found by returning to the original geometry as shown in FIGS. 10A and 10B which illustrate the conical angle $\beta_{ij}$ for the central detector column $j_0$ and the jth detector column respectively of detector row i.

In terms of $h_i$ and r:

$$\beta_i = \tan^{-1}(h_i/r). \tag{21}$$

The conical angle $\beta_i$ is the same for all channels of the original fan-beam projections $P_{ij}$ within the same transaxial fan, because $h_{ij}=h_{ij_0}=h_i$.

Since each row of the reordered parallel-beam projections $R_{ij}$ is reordered from the same row of fan beam projections $P_{ij}$ at different rotation angles $\theta$, they each have the same conical angle $\beta_i$. Combining Equations 12 and 21 gives:

$$\beta_i = \tan^{-1}((i-i_o)*\Delta h/r) \tag{22}$$

Since the constant-z interpolated projections $S_{ij}(\phi)$ are interpolated from the parallel-beam projections $R_{i'j}(\phi)$, with i' depending on the channel j, the conical angle $\beta_{ij}$ of $S_{ij}(\phi)$ varies with the row number i as well as the column number j. For the jth column in the ith row, the conical angle of $S_{ij}(\phi)$ is $$\beta_{ij} = \tan^{-1}((i'-i_o)*\Delta h/r)$$

Substituting i' from Equation 18, the conical angle becomes $$\beta_{ij} = \tan^{-1}((i-i_o)*\Delta h/r+(j-j_o)*\delta*D/(a_j*\pi)) \tag{23}$$

If the conical angles $\beta_{ij}$ were zero for all detectors in all rows, reconstruction would be as accurate as in the conventional system. The non-vanishing conical angles $\beta_{ij}$ introduce reconstruction errors to the image. However, it does not make much difference in the extent of the reconstruction errors whether the conical angles are equal in the same row or if they vary gradually from channel to channel as in Equation 23, providing the magnitudes of the conical angles are in the same range. The reconstruction errors are mainly determined by the magnitude of deviation of the projection path from the reconstructing slice plane, regardless of whether the deviation occurs within the same view or different views.

Figure 11:
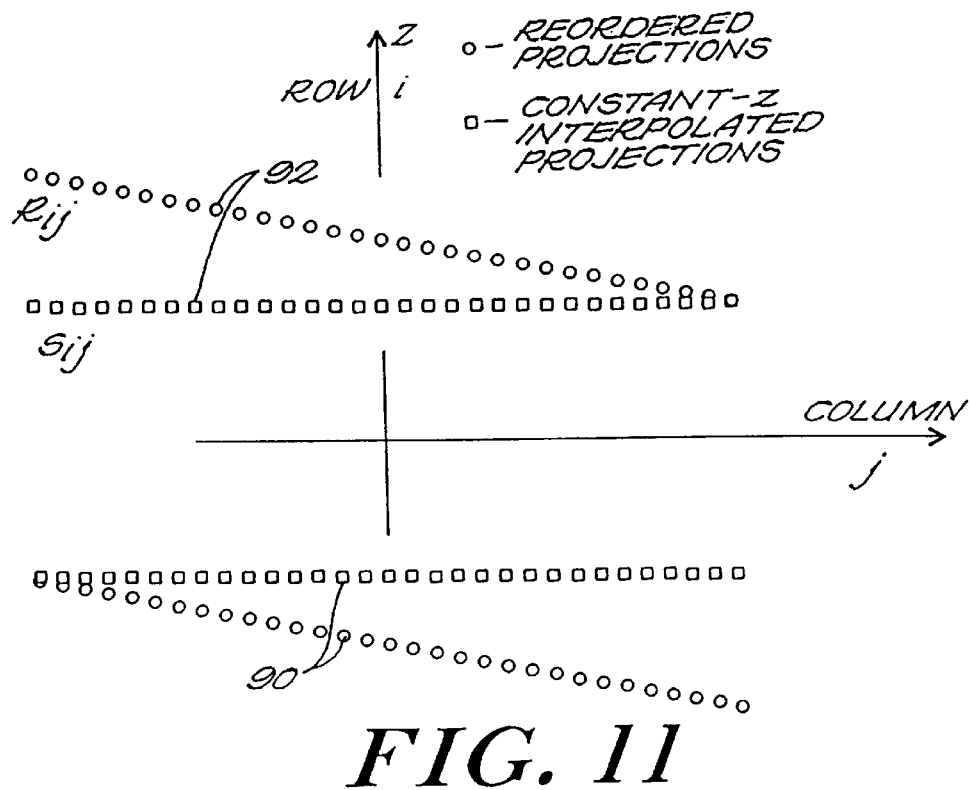
FIG. 11 is an illustration of the z positions of the first- and last-row projection data prior to and following constant-z interpolation in accordance with the present invention.

Since the constant-z interpolated projections $S_{ij}$ are interpolated from the reordered projections $R_{ij}$, the interpolated projections $S_{ij}$ have a smaller positional range in z dimension than the reordered projections $R_{ij}$. FIG. 11 is a plot of the z-positions of the first row 90 and last row 92 of $R_{ij}$ and $S_{ij}$ at a view angle $\phi$. To have valid interpolated projections $S_{ij}$ for all columns, the number of rows for the constant-z interpolated projections $S_{ij}$ must be smaller than that of the reordered projections $R_{ij}$, assuming the same spacing between adjacent rows. If the original number of rows for $R_{ij}$ is M, and the reduced number of rows for $S_{ij}$ is m, the longest translation distance D for either a full-scan or a half-scan will be $$D=m*\Delta h \tag{24}$$

where m<M. Thus, to ensure all interpolated constant-z projections $S_{ij}$ are within the scanning range, the maximum pitch is preferably D, as given in Equation 24 for a full-scan system, and 2D for a half-scan system.

IV. Interpolation for Equal Spatial Intervals

Interpolated constant-z projections $S_{ij}(\phi)$ are derived from original projections which are separated by a constant angular interval $\delta$ in the transaxial fan, as given in Equation 3 for a cylindrical detector array. Although the original projections have been reordered into parallel projections $R_{ij}$ in xy space, the spatial intervals between adjacent projections are unequal, contrary to preferred parallel-beam reconstruction techniques where the spacings should be equal. It is therefore preferable to interpolate the constants interpolated projections $S_{ij}(\phi)$ a second time, such that the resulting equal-spaced projections $T_{ij}(\phi)$ have an equal spatial interval d for every row.

Figure 12:
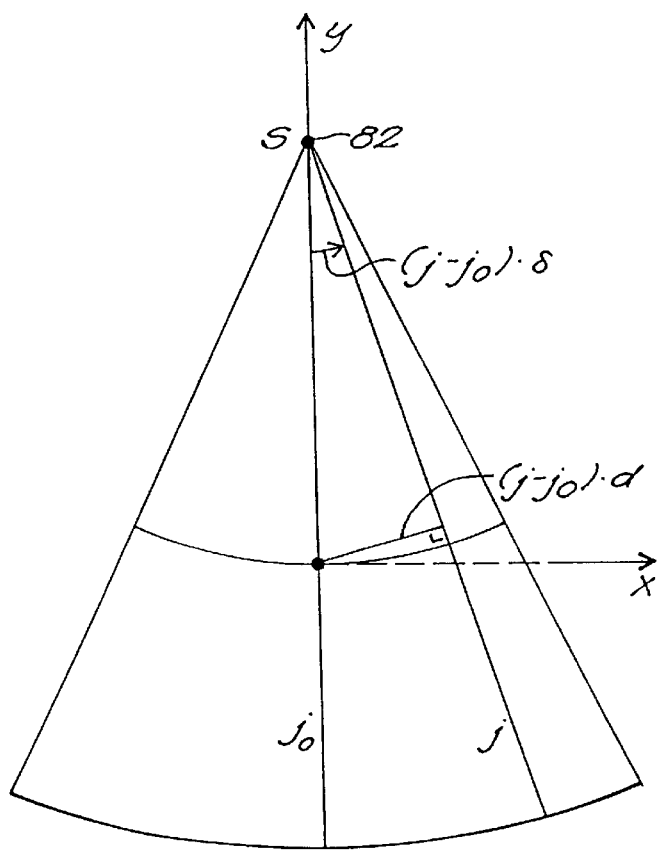
FIG. 12 illustrates the spatial distance and angular distance of a projection path from the central projection, in accordance with the present invention.

To interpolate for detector column j of the equal spaced projections $T_{ij}(\phi)$, the corresponding column j' in the interpolated constant-z projections $S_{ij'}(\phi)$ can be calculated from the following relationship:

$$(j-j_o)*d=r*\sin(j'-j_o)*\delta) \tag{25}$$

where $j_o$ is the central column shown in FIG. 12. Rearranging Equation 25, gives:

$$j'=j_o+\sin^{-1}((j-j_o)*d/r)/\delta. \tag{26}$$

It is preferable to use the spacing between the central column and its adjacent channel, that is the spatial interval between the projections $S_{ij_o}(\phi)$ and $S_{i,j_o+1}(\phi)$, as the constant d.

Based on Equation 26, equal-spaced projections $T_{ij}(\phi)$ are interpolated from the interpolated constant-z projections $S_{ij}(\phi)$ for each row i at each view angle $\phi$. High order interpolations are preferred for this calculation, for example the well-known four-point or six-point Everett interpolation.

V. Convolution

The next step in the inventive technique is the convolution of the equal-spaced projections $T_{ij}(\phi)$. Just like the two-dimensional reconstruction in a conventional scanner of single-row detector system, the equal-spaced projections $T_{ij}(\phi)$ are oversampled in the low-frequency components from different view angles. For example, the DC component of $T_{ij}(\phi)$ represents the sum of all projections in the ith row, which is the total mass of the object being illuminated by the X-ray beams of the ith row. If the conical angles $\beta_{ij}$ are zero as in the two-dimensional reconstruction case, the DC component of $T_{ij}(\phi)$ in each row would be the same for all view angles $\phi$. The other low-frequency components are not as redundant as the DC component, but nevertheless they are oversampled. The convolution operates as a high-pass filter which de-emphasizes the low-frequency components to equalize the sampling in the two-dimensional frequency space for backprojection.

The original projections do not illuminate the same plane of the object as the view angle changes due to non-vanishing conical angles $\beta_{ij}$ and the translation along the z-axis. But for projections $T_{ij}(\phi)$, which have been interpolated to a constant-z-position, the projections are only slightly deviated from the xy plane at that z-position if the conical angles $\beta_{ij}$ are small. In other words, for small conical angles, the sampling in two-dimensional frequency space approximates the case of a zero conical angle. For small conical angles, it is a good approximation to use the same convolution kernel as a conventional two-dimensional parallel-beam reconstruction.

In view of this, in a preferred embodiment of the present invention, the equal-spaced projections $T_{ij}(\phi)$ are filtered with a conventional convolution kernel to provide filtered projections $U_{ij}(\phi)$ for each row i at each view angle $\phi$. The filtered projections $U_{ij}(\phi)$ are later used for backprojection.

To appreciate the effects of convolution, consider a back-projected point spread function without convolution. If the intensity data of the sensed object is negligible everywhere except at a single point, the image intensity resulting from the backprojection will peak at this point, and distribute to surrounding regions. The high-pass convolution kernel applied to the projections sharpen this point spread function. The filtering kernel is preferably a narrow sinc function in the spatial domain. Its amplitude peaks at the center and drops off rapidly toward both sides. Therefore, it is important to keep the nearby projections on the same plane for the filtering kernel to work properly. However, those projections at a location far from the center point can be slightly deviated from the plane, since they do not have much response to the high-pass filtering kernel.

VI Three-Dimensional Backprojection

A. Overview

Following convolution, the filtered projections $U_{ij}(\phi)$ are backprojected along their corresponding X-ray beam paths to form a three-dimensional volumetric image. Due to the conical angle $\beta_{ij}$, each voxel is, in general, backprojected from different rows of filtered projections $U_{ij}(\phi)$ at different view angles $\phi$. Since a voxel does not lie exactly on the projection path of a detector, the data for backprojecting to the voxel should be interpolated from the filtered projections $U_{ij}(\phi)$ of adjacent columns and adjacent rows. Furthermore, in a helical scan, successive sections of the object along the z-direction are continuously scanned. The data is grouped and processed in a certain sequence, such that the volumetric images can be reconstructed section-by-section in a continuous and orderly manner.

Consider a coordinate system xyz which rotates with the gantry, but translates with the object. It is the equivalent to envision that under this coordinate system the object is rotating about the z-axis and the gantry is translating along the z direction. The axial projection paths of the central column $j_o$ are plotted on the yz plane in FIGS. 13A, 13B, 13C under this coordinate system. The axial fans of other columns j also lie along yz planes but at different x positions.

Figure 13C:
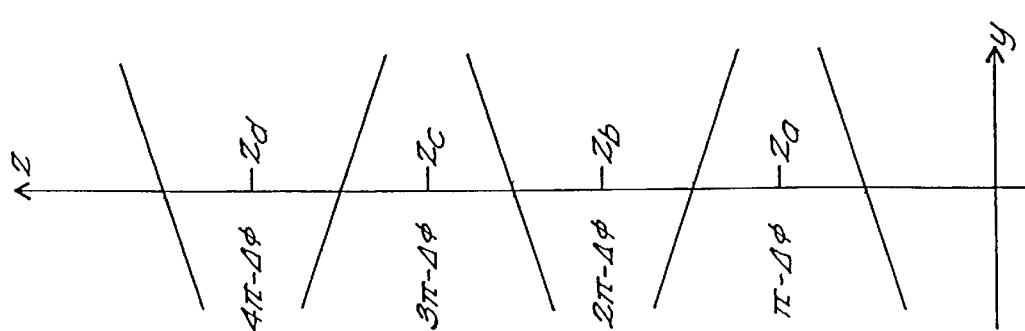
FIGS. 13A, 13B and 13C illustrate axial projections from a plurality of view angles, translated with respect to the z-axis in accordance with the present invention.
Figure 13B:
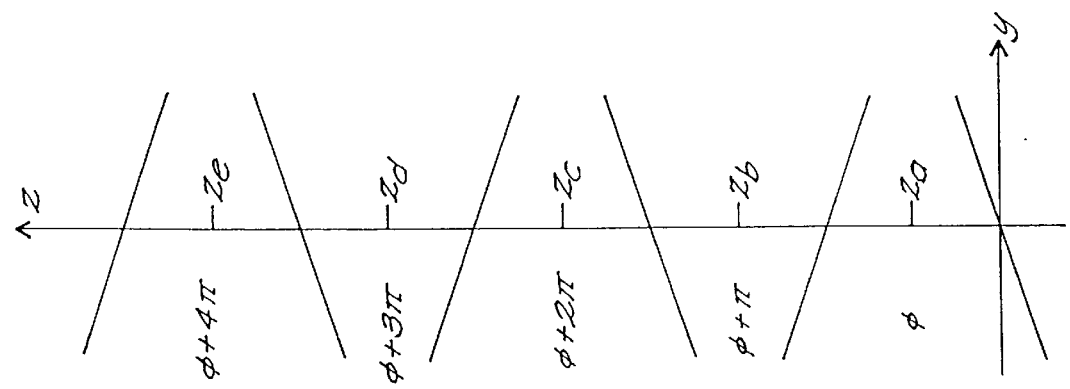

In FIG. 13B, the projection paths from view angles $\phi$, $\phi+\pi$, $\phi+2\pi$, $\phi+3\pi$ are superimposed. The projection data for these four view angles were acquired at every half rotation when the gantry center is at the z-position of $z_a$, $z_b$, $z_c$, and $z_d$. These z-positions are separated by a constant distance D, equal to half of the pitch, or half the translation distance per rotation of the system. Because of the half-rotation difference, the paths for the view angles $\phi$ and $\phi+2\pi$ are plotted in the reverse y-axis direction with respect to the view angles $\phi+\pi$ and $\phi+3\pi$.

Figure 13A:
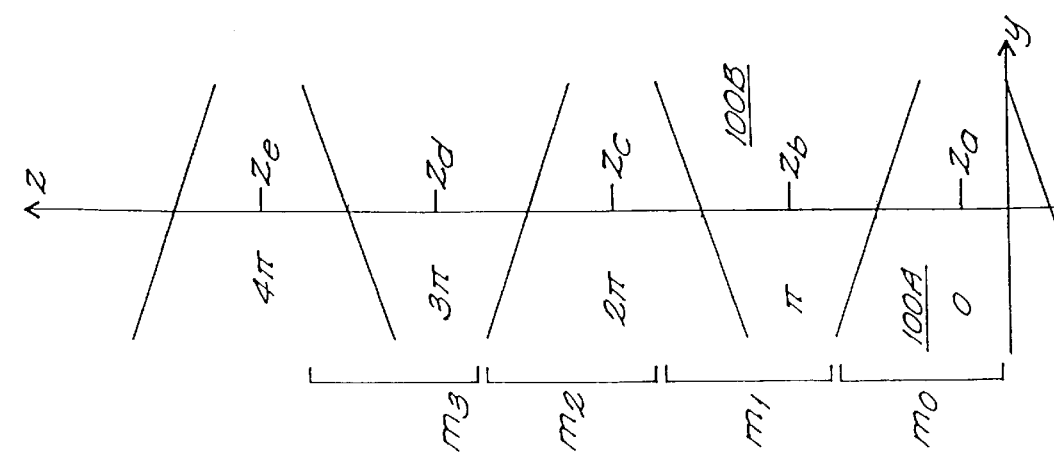

The volumetric image is divided into sections $m_0$, $m_1$, $m_2$, $m_3$, etc . . . , each section including the same number of object slices, m, but located at different z-positions. FIG. 13A is the superimposed projection paths at multiples of the first view angle 0, $\pi$, $2\pi$, $3\pi$; while FIG. 13C represents the last view angle for reconstructing the sections $\pi-\Delta\phi$, $2\pi-\Delta\phi$, $3\pi-\Delta\phi$, . . . , where $\Delta\phi$ is the view-angle interval. The division of the sections has the same repetition as the axial fans. As the result, each section can be backprojected in the same manner. A three-dimensional matrix is used to backproject for one section. When the three-dimensional matrix is reconstructed from superimposed projections of view angles ranging from 0 to $\pi-\Delta\phi$, then the same three-dimensional matrix will be used for reconstructing the next section.

The backprojection for section $m_1$, for example, requires two axial fans centered at $z_c$ and $z_b$ for each column in the initial view angles. At view angle $\phi$, it further requires data for the axial fan centered at $z_a$. Thus, two to three axial fans per column are required for back projecting each section $m_0$ . . . . $m_3$ at a view angle. It is possible to reduce the requirement to no more than two axial fans by reducing the number of slices per section without changing the slice width. However, because some computations can be shared among these slices, the overall efficiency of the backprojection will be improved with more slices in a smaller number of sections.

B. Overlapping of Axial Fans-Separation Line

The boundary 102 between two superimposed axial fans for example fans 100A and 100B may be slightly overlapped. The extent of overlapping depends on the manner in which the reordered projections $R_{ij}(\phi)$ are interpolated into the constant-z projections $S_{ij}(\phi)$, and also depends on the pitch D used for the helical scan. If the midpoint $c_{ij}$ described above is used to measure the z-position of the projection and the translation distance is D=m*$\Delta$h as given in Equation 24 over a half rotation of the gantry, the two superimposed axial fans of $S_{ij}(\phi)$ will be perfectly matched without overlapping in every detector column. This is a significant advantage of using the midpoint $c_{ij}$ as the reference point for the constant z-position interpolation.

The distribution of $S_{ij}(\phi)$, $S_{ij}(\phi+\pi)$, and $S_{ij}(\phi+2\pi)$ for the central detector column and a detector column located at a distance from the center are shown in FIGS. 14 and 15 respectively in yz-space. The locations of constant-z interval $\Delta$h are all on the z-axis for $S_{ij}(\phi)$, $S_{ij}(\phi+\pi)$, $S_{ij}(\phi+2\pi)$.

Figure 16:
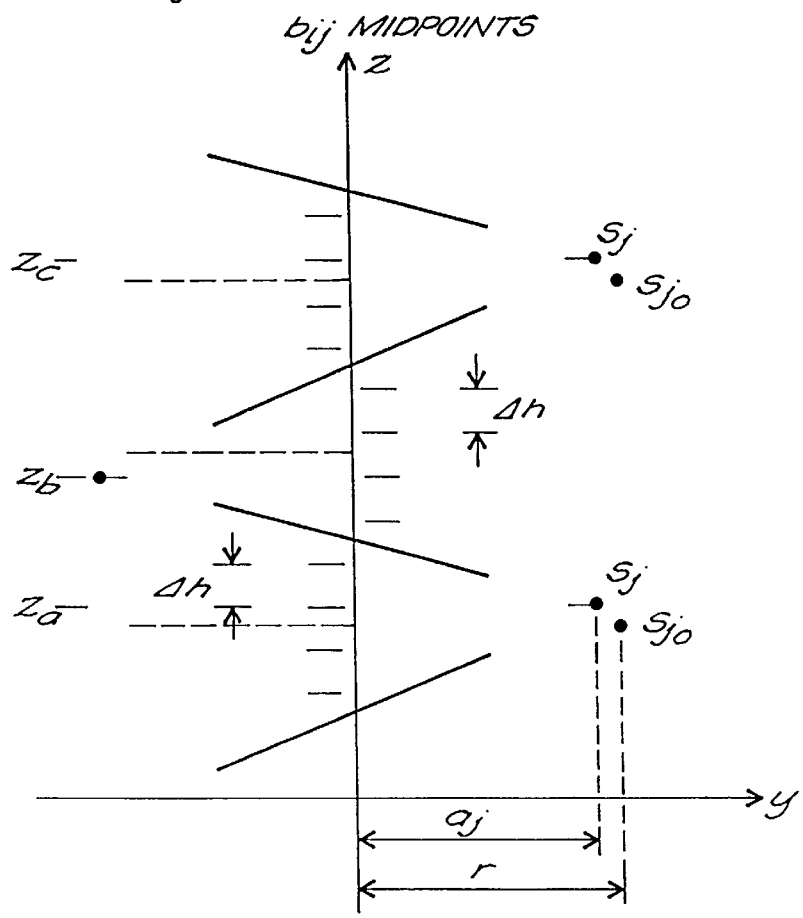
FIG. 16 illustrates the distribution of constant-z interpolated projections $S_{ij}(\phi)$ for a detector column located a distance from the central column, using $b_{ij}$ as the midpoint for purposes of the interpolation, in accordance with the present invention.

If the point $b_{ij}$ of FIG. 9 is used as the reference point for the constant-z interpolation in an alternative embodiment, the distribution of $S_{ij}(\phi)$ for a detector column located far from the central column is illustrated in FIG. 16 for comparison. Unlike that based on the midpoint $c_{ij}$ in FIG. 15, the locations of constant-z intervals $\Delta$h do not lie on the xz-plane, i.e., y=0, although the distribution for the central column remains the same as in FIG. 14. The inferior distribution of constant-z positions not only requires more computations but also results in less accurate backprojection for the voxels located near the boundary regions.

Figure 17:
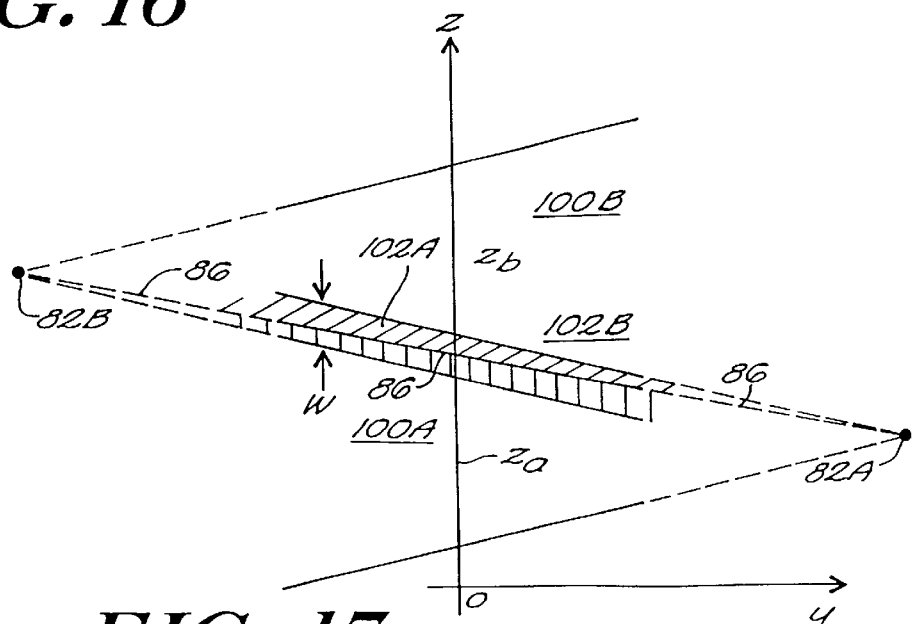
FIG. 17 illustrates the opposing axial fans, where W is the width of the overlapping region and a separation line which limits the extent of each fan for backprojection in accordance with the present invention.

When the pitch is shorter, for example where D<m*$\Delta$h, there will be overlapping in the boundary regions 102. Whether scanning with a pitch of perfect match of the two superimposed axial fans, or a shorter pitch, a separation line 86 is used across the boundary region to separate the axial fans 100A, 100B for backprojection. It is preferable to select the line connecting the two axial-fan sources 82A, 82B as the separation line, as illustrated in FIG. 17 with a slightly overlapped region 102.

The projections of either axial fan 100A, 100B beyond this separation line 86 will not be used for backprojection. For example, the projections corresponding to overlapping region 102A, a portion of axial fan 100A, and projections corresponding to overlapping region 102B, a portion of fan 100B, are removed from consideration. Under this arrangement, the projections within the overlapped region 102A, 102B are uniquely defined. At a view angle $\phi$, a voxel will be located on either side of this separation line 86, and only the projection value from that side of axial fan will be backprojected to the voxel.

The separation lines 86 for different columns are not parallel to each other, because the z-position of the axial fan is column-dependent. Suppose at a given view angle $\phi$ the z-positions of the two opposed axial-fan sources are $z_a$ and $z_b$ as indicated in FIG. 17. The difference between $z_a$ and $z_b$ can be obtained from Equation 16 by letting $i=i_o$ and noting that the columns in filtered projections $U_{ij}(\phi+\pi)$ are in reverse order with respect to $U_{ij}(\phi)$:

$$z_b - z_a = D + 2\delta^*(j - j_o)^* D/\pi \quad (27)$$

The middle position between $z_a$ and $z_b$ can also be obtained from Equation 16 by replacing $\phi$ with $\phi+\pi$ for $z_b$ and setting $i=i_0$, $$(z_b + z_a)/2 = D/2 + \phi^* D/\pi \quad (28)$$

Using Equations 27 and 28, the z-coordinate of the separation line $z_{sj}$ can be calculated as a function of the y-coordinate from $$z_{sj} = (z_b + z_a)/2 - y^*(z_b - z_a)/2a_j \quad (29)$$

In Equations 29 and 16, the position of the central row of $U_{ij}(\phi)$ is at $z=0$ when $\phi=0$. That is $z_{sj}=0$ when $\phi=0$. An offset $z_o$ is added to Equation 26 in general cases as $$z_{sj} = z_o + (z_b + z_a)/2 - y^*(z_b - z_a)/2a_j \quad (30)$$

where $z_o$ is the $z_a$ value at view angle $\phi=0$, and $a_j$ is given by Equation 9.

C. Backprojection in Two Stages

The next step of the inventive process involves backprojection in two stages, each involving an interpolation. The first interpolation stage is based on the x position of the voxels. The corresponding column $j_x$ is calculated and the filtered projection value $U_{ij_x}$ is interpolated from adjacent columns $U_{ij}$ and $U_{ij+1}$, where $j \leq j_x < j+1$, for each row of the superimposed projections. The second stage is based on the y and z-positions of each voxel. The corresponding row $i_z$ of the projection passing through the location (y,z) is calculated and the projection value $U_{i,jx}$ is interpolated from $U_{ij_x}$ and $U_{i+1,jx}$, with $i \leq i_z < i+1$. The bilinear interpolated projection $U_{ij_x}$ is then preferably used to backproject for the voxel.

Figure 18:
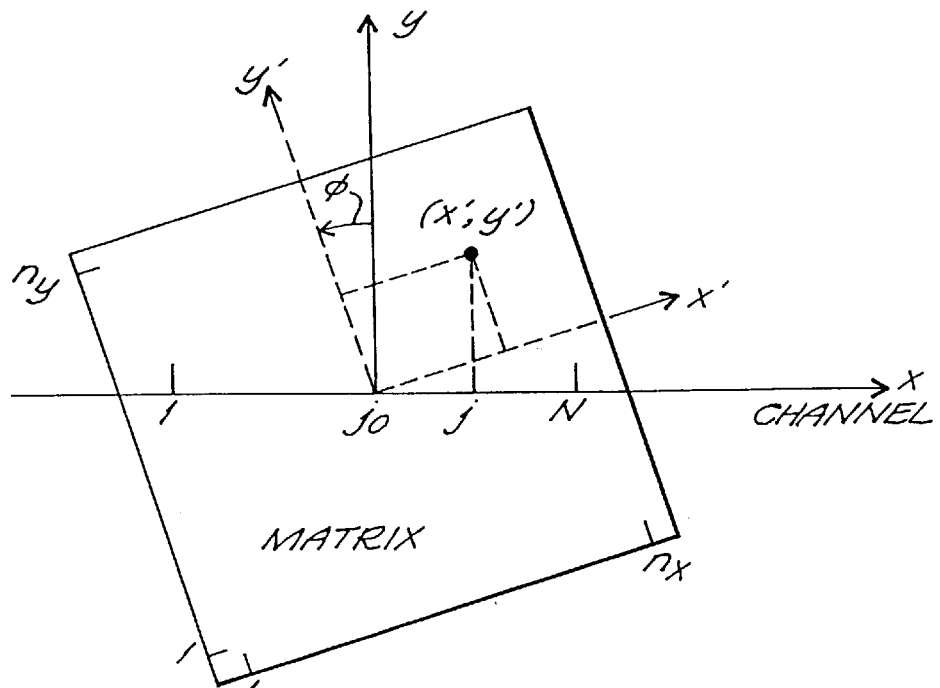
FIG. 18 illustrates reconstruction of a section of the object in a coordinate system (x',y',z') fixed in object space, and illustrates the geometry of the first stage interpolation of backprojection in accordance with the present invention.

To reconstruct a section of the object, a coordinate system x'y'z' fixed in the object space is used as shown in FIG. 18. Assuming there are m slices on the x'y' planes in the three-dimensional matrix of voxels representing the object. For a view angle $\phi$, this coordinate system is rotated about the z'-axis with respect to the coordinate system xyz for the angle $\phi$, with the z'-axis coincides with the z-axis. The location of a voxel with respect to the gantry, that is the coordinate (x,y), can be calculated from the location of the voxel in the object coordinate (x',y'). The z-positions are not changed by the rotation, and those voxels with the same (x',y') locations from different slices will have the same (x,y) coordinate.

D. First Stage Interpolation

The first-stage interpolation in the x-dimension for $U_{ij_x}$ is commonly used in the conventional two-dimensional parallel-beam reconstruction. If (x',y',z') is the coordinate of a voxel at rotation angle of $\phi$, then $$x = x' \cos(\phi) + y' \sin(\phi)$$

$$y = y' \cos(\phi) - x' \sin(\phi)$$

$$z = z' \quad (31)$$

FIG. 18 illustrates the coordinate (x,y) of a voxel located at (x',y'). The coordinate x is converted to a corresponding column number $$j_x = j_o + x \quad (32)$$

where $j_o$ is the central column number. The interpolated projection can be calculated by linear interpolation as $$U_{ij_x} = (j+1-j_x)^* U_{ij} + (j_x - j)^* U_{ij+1} \quad (33)$$

where $j \leq j_x < j+1$.

Figure 19:
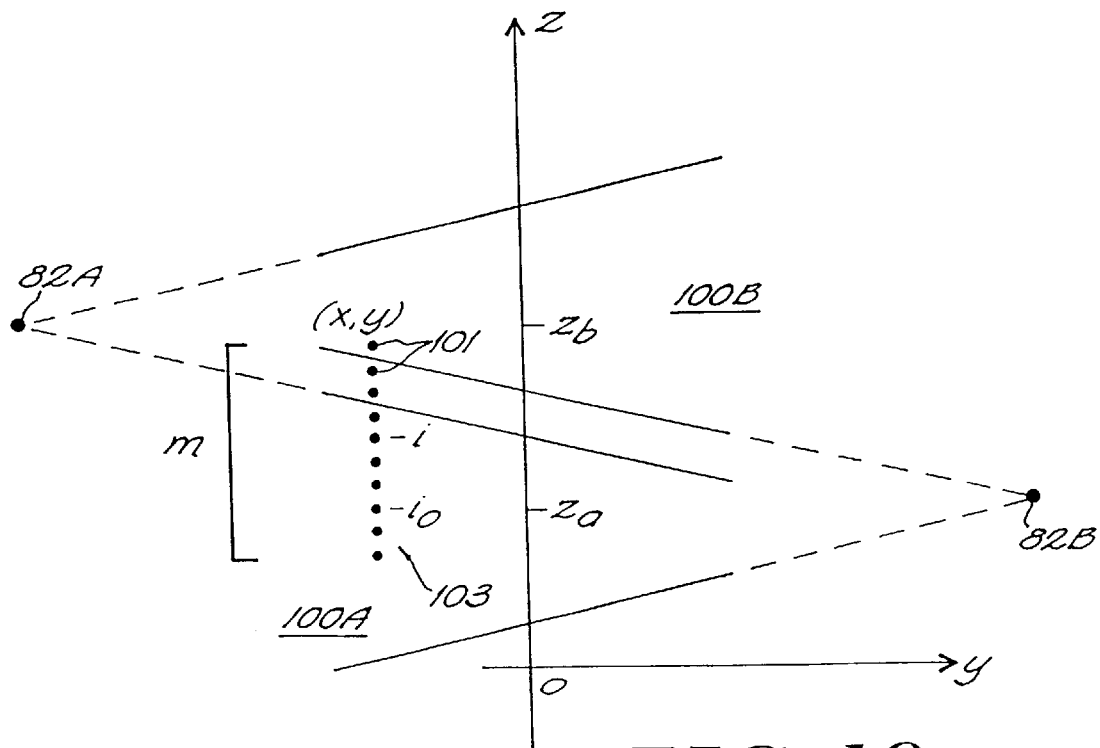
FIGS. 19, 20A and 20B illustrate the geometry of second stage interpolation of backprojection in accordance with the present invention.

The interpolation is performed for both superimposed axial fans. In other words, Equation 33 is used to interpolate for $U_{ij_x}(\phi)$ 100A and $U_{ij_x}(\phi+\pi)$ 100B which lies within the z dimension of the matrix. For example, a column of voxels 103 with the same (x,y) coordinates but different z-coordinates are marked in dots in FIG. 19. In this example, most of these voxels will be backprojected from $U_{ij}(\phi)$ 100A, but the two voxels 101 at the highest z-coordinate will be backprojected from $U_{ij}(\phi+\pi)$ 100B.

Figure 20A:
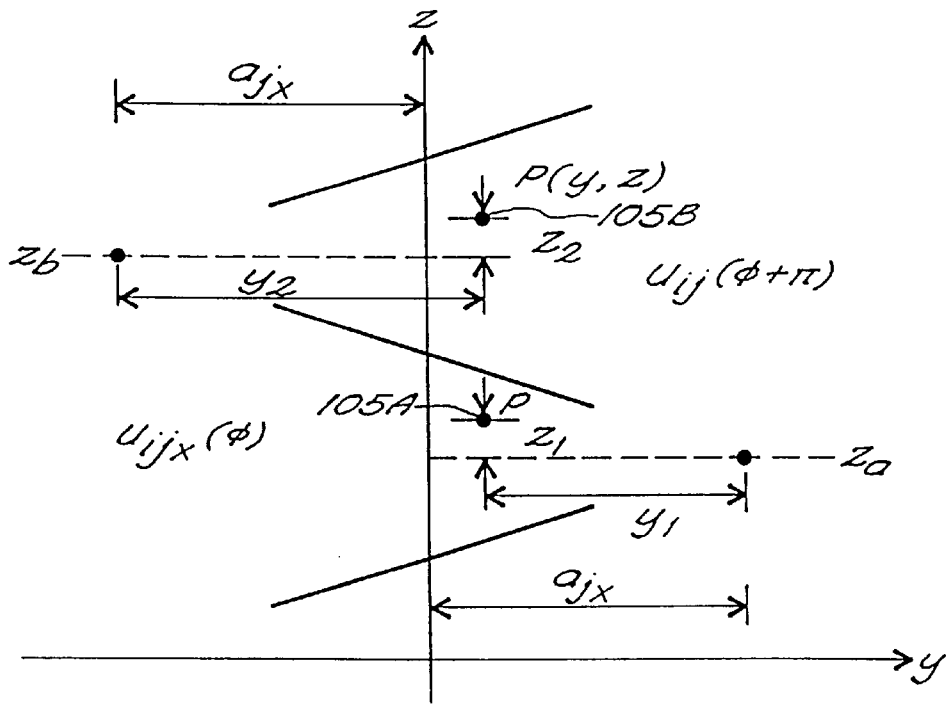

E. Second Stage Interpolation The second-stage interpolation for $U_{ij_x}$ in yz space is more sophisticated than the first stage. Given the coordinate (y,z) of a voxel, the corresponding row number $i_z$ of the projection $U_{ij_x}$ which passes through the voxel must first be determined. This row number $i_z$ can be calculated from the z position of the projection $U_{ij_x}$, that is the z-axis intercept of $U_{ij_x}$. Let $y_1$ and $z_1$ represent the distance of the voxel 105A measured from the X-ray source of $U_{ij_x}(\phi)$ diverging from a focal point at a positive y-axis position of $y_a = a_{jx}$, as shown in FIG. 20A. Similarly, let $y_2$ and $z_2$ represent the distance from the voxel 105B measured from the X-ray source of $U_{ij_x}(\phi+\pi)$ diverging from a focal point at a negative y-axis position of $y_b = -a_{jx}$. From this figure it is clear that $$y_1 = a_{jx} - y \quad (34)$$

$$z_1 = z - z_a$$

for $U_{ij_x}(\phi)$ and $$y_2 + a_{jx} + y \quad (35)$$

$$z_2 = z - z_b$$

for $U_{ij_x}(\phi+\pi)$.

Figure 20B:
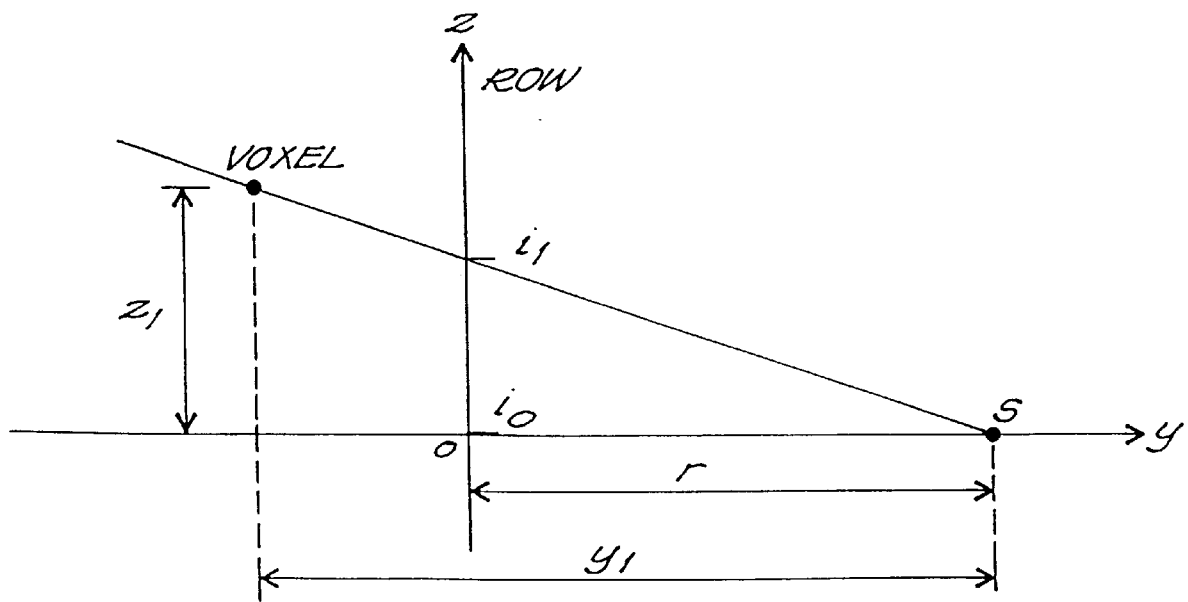

The X-ray paths are separated by equal spatial intervals when they are measured along the z direction. FIG. 20B illustrates the $U_{ij_x}(\phi)$ projection path passing through the voxel at $(y_1, z_1)$. The intercept of the path on the z-axis is $$i_1 - i_{o1} = z_1 * a_{jx} / y_1 \quad (36)$$

where $i_{o1}$ is the central row number of $U_{ij_x}(\phi)$. Equation 36 provides the increment of row number with respect to increment in z-coordinate of the voxel, $$\Delta i_1 = \Delta z_1 * a_{jx}/y_1 \qquad (37)$$

If the z-dimension of the matrix is chosen to be the same spacing as the intercept of X-ray paths on the z-axis, then $\Delta z_1 = 1$. The row increments for $U_{ij_x}(\phi)$ and $U_{ij_x}(\phi+\pi)$, respectively become $$\Delta i_1 = a_{jx}/y_1$$

$$\Delta i_2 = a_{jx}/y_2 \qquad (38)$$

For fast computation, $\Delta i_1$ and $\Delta i_2$ can be obtained from a lookup table based on $y_1$ and $y_2$.

The location of $z_{sjx}$ of the separation line between these two axial fans can be calculated from Equations 27, 28, and 30, by using $j=j_x$ and y from Equation 31.

For voxels with z locations of $0 \leq z < z_{sjx}$, the axial fan $U_{ij_x}(\phi)$ is interpolated for backprojection. The interpolating row number is computed from $$i_z = i_{o1} + z_1 * \Delta i_1 \qquad (39)$$

with $z_1$ and $\Delta i_1$ given by Equations 34 and 38.
The final projection value for backprojection is then $$U_{ij_x}(\phi) = (i+1-i_z)*U_{ij_x}(\phi) + (i_z-i)*U_{i,j+1}(\phi) \qquad (40)$$

where $i \leq i_z < i+1$

For voxels with z locations of $z_{sjx} \leq z < m$, the other axial fan $U_{ij_x}(\phi+\pi)$ will be interpolated for backprojection. The interpolating row number is computed from $$i_z = i_{o2} + z_2 * \Delta i_2 \qquad (41)$$

where $i_{o2}$ is the central row number of $U_{ij_x}(\phi+\pi)$. The final projection value for backprojection is $$U_{i_z j_x}(\phi) = (i+1-i_z)*U_{ij_x}(\phi+\pi) + (i_z-i)*U_{i,j+1}(\phi+\pi) \qquad (42)$$

with $i \leq i_z < i+1$

F. Computing Algorithm for Vector Processing

Figure 21:
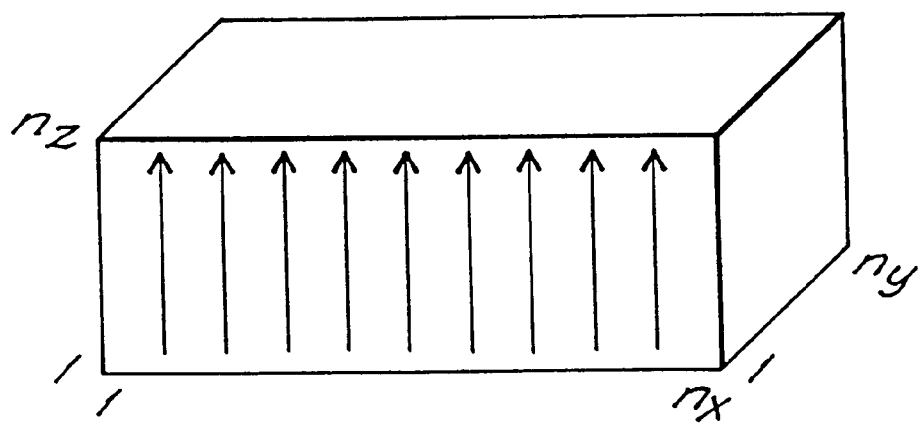
FIGS. 21 and 22 illustrate the relative inefficiency of first back projecting voxels along the z' dimension, and the relative efficiency of first back projecting the x' dimension, respectively, in accordance with the present invention.

Suppose the dimensions of the three-dimensional matrix are $n_x$, $n_y$, and $n_z$. In the computing sequence described above, all voxels with the same (x', y') coordinate are backprojected first. At the innermost loop of the computing sequence, the z' dimension is most computationally active as shown in FIG. 21. However, the $n_z$ dimension is usually small when compared to $n_x$ or $n_y$ dimensions in this application. Although it is more comprehensible, this sequence is not necessarily the most efficient for computing the three-dimensional backprojection.

Figure 22:
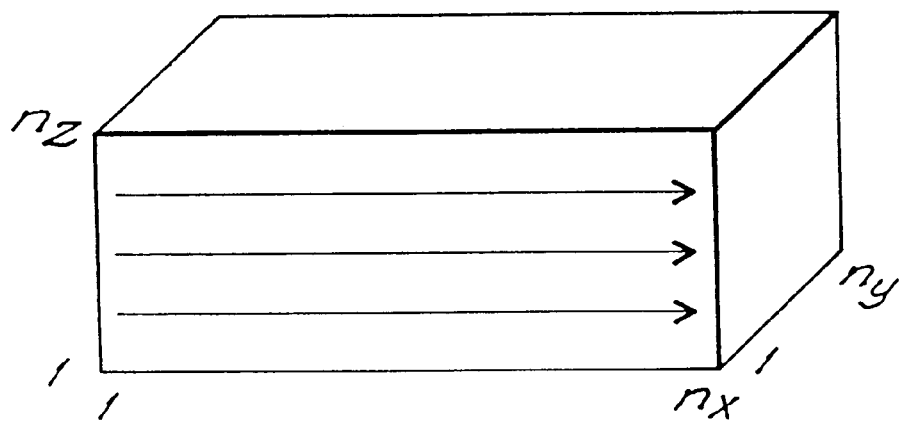

To achieve more efficient, and therefore faster backprojection, the x' dimension (or the y' dimension) is selected as the innermost computation loop, or the first running dimension. In this preferred sequence, all voxels along x' direction with the same (y',z') coordinate are backprojected first. The z' dimension becomes the second running dimension as shown in FIG. 22. Most computations are therefore processed as one-dimensional array with $n_x$ being the array size.

For the first stage interpolation, the (x,y) coordinates are calculated for x'-dimension as in Equation 31, $$x[k] = x'[k]*\cos(\phi) + y'*\sin(\phi)$$

$$y[k] = y'*\cos(\phi) - x'[k]*\sin(\phi) \qquad (43)$$

with $k=1, 2, \ldots, n_x$.
The array index k is related to the x' coordinate by $$k = x' + (n_x+1)/2 \qquad (44)$$

Equations 32 and 33 become $$j_x[k] = j_o + x[k] \qquad (45)$$

$$U_{ij_x[k]} = (j+i-j_x[k])*U_{ij} + (j_x[k]-j)*U_{i,j+1} \qquad (46)$$

with $j \leq j_x[k] < j+1$ and $k=1, 2, \ldots n_x$.

Equation 46 is used for both $U_{ij_x[k]}(\phi)$ and $U_{ij_x[k]}(\phi+\pi)$. The total number of interpolations for each y' is $n_x n_z$.

For the second stage interpolation, the position of the voxels with respect to the X-ray sources are:

$$y_1[k] = a_{jx[k]} - y[k]$$

$$y_2[k] = a_{jx[k]} + y[k] \qquad (47)$$

by using Equations 34 and 35 in array form for $k=1, 2, \ldots, n_x$, and $$z_1 = z' - z_a$$

$$z_2 = z' - z_b \qquad (48)$$

Notice that z'=z from Equation 31. The row number increments are calculated in array form of Equation 37 as $$\Delta i_1[k] = \Delta z_1 * a_{jx[k]}/y_1[k]$$

$$\Delta i_2[k] = \Delta z_2 * a_{jx[k]}/y_2[k] \qquad (49)$$

This approach handles the voxels as an array of voxels in the x' dimension. Although it is possible to determine the location where these voxels cross over the separation line of the two superimposed axial fans, the computation is time consuming. Instead, it is preferable to pre-calculate the index $k=k_s$ where the voxels cross over the separation line. This index $k_s$ can be tracked down from the procedure in the z'-dimension backprojection, as described by Equations 39 through 42, where each voxel is known to be in the region of either $U_{ij_x}(\phi)$ or $U_{ij_x}(\phi+\pi)$ for backprojection. In total, there are $n_y n_z$ values of $k_s$ to be pre-calculated and stored as a lookup table for each view angle. During reconstruction, each $k_s$ will be read from the table to determine whether the array of elements is falls into the region of $U_{ij_x}(\phi)$, or $U_{ij_x}(\phi+\pi)$, or both.

For $0 \leq k < k_s$, projections of the axial fan $U_{ij_x[k]}(\phi)$ are used for the second stage interpolation with the row number similar to Equation 39

$$i_z[k] = i_{o1} + z_1 * \Delta i_1[k] \qquad (50)$$

and the final value for backprojection is $$U_{ij_x}[k](\phi) = (i+1-i_z[k])*U_{ij_x}[k](\phi) + (i_z[k]-i)*U_{i,j_x}[k]+1(\phi) \qquad (51)$$

with $k=1, 2, \ldots, n_x$, and $i \leq i_z[k] < i+1$

For $k_s<k \leq n_x$, projections of the axial fan $U_{ij_x}[k](\phi+\pi)$ are used for the interpolation with the row number $$i_z[k]=i_{o2}+z_2*\Delta i_2[k] \qquad (52)$$

and the final value for backprojection is $$U_{i,j_x}[k](\phi)=(i+1-i_z[k])*U_{ij_x}[k](\phi+\pi)+(i_z[k]-i)*U_{i,j_x}[k]+1(\phi+\pi) \qquad (53)$$

with k=1, 2, . . . ,nx. and $i \leq i_z[k]<i+1$

With the data arranged in long arrays, the overhead time required for accessing the data and executing the computations are substantially reduced, and the overall speed of the backprojection process is greatly enhanced. This technique is especially amenable for use with a high-speed array processor or a special-purpose computer designed for backprojection.

Figure 23A:
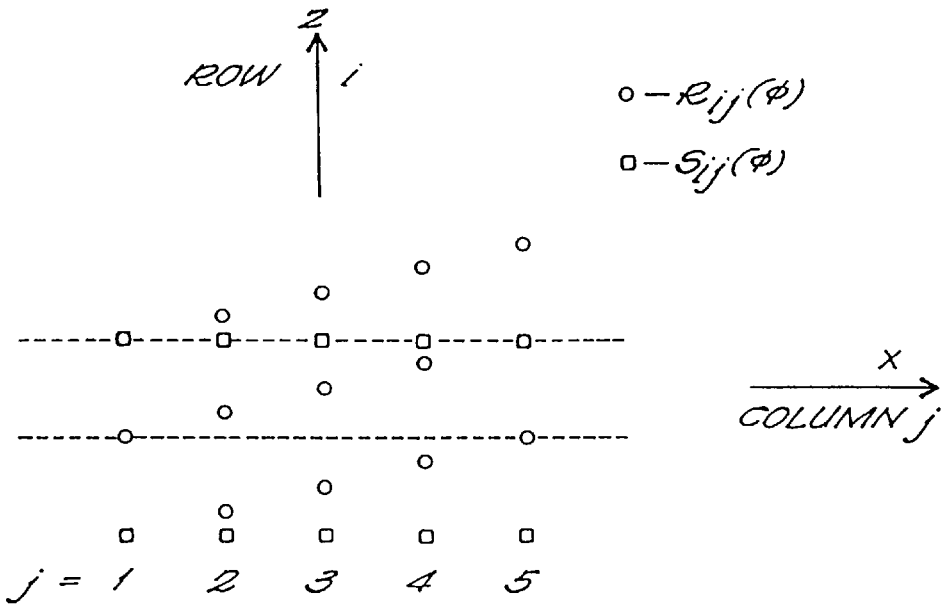
FIG. 23A is an illustration of the parallel projections $R_{ij}$ interpolated into constants interpolated projections $S_{ij}$.

VII. Improved Approaches for Constant-z Interpolation The constant-z interpolation is an important operation of the present invention. However, there is a slight degradation of image resolution along the z-direction as a result. This arises from to the fact that the interpolation behaves as a low-pass filter. The filtering effect depends on how far the interpolation point is located from the original data point. This is illustrated in FIG. 23A for a small section of the reordered projection data $R_{ij}(\phi)$ marked in circles. The locations of the constants interpolated projections $S_{ij}(\phi)$ are marked in squares. In this example, the interpolated points for column 1 and column 5 coinciding with the original data points exactly, i.e., $S_{i1}=R_{i1}$ and $S_{i5}=R_{i5}$. There is no filtering effect on these two columns at all. But columns 2 and 4, and particularly column 3, are degraded in resolution because $S_{i3}$, for instance, is at the halfway point between $R_{i3}$ and $R_{i-1,3}$.

Figure 23B:
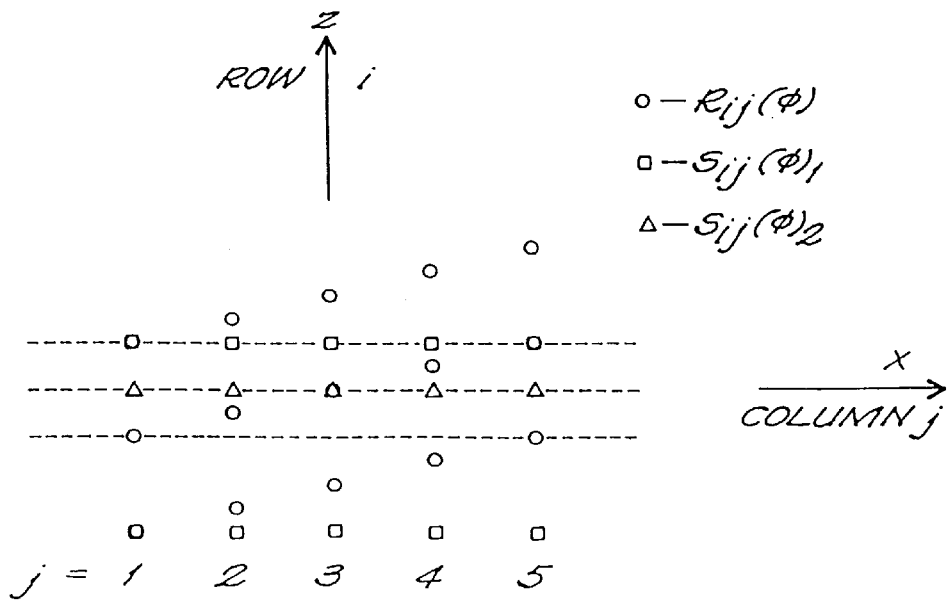
In FIG. 23B, the number of interpolation points is doubled.

This degradation can be reduced if more rows are interpolated. For example, if 2M rows of interpolated projections $S_{ij}(\phi)$ are interpolated from M rows of reordered projections $R_{ij}(\phi)$ at half-spatial intervals, the effect of low-pass filtering will be reduced by a factor of two. In FIG. 23B, another row of interpolated projections $S_{ij}(\phi)_2$ are added, marked in triangles. In this illustration, every other row of interpolated projections $S_{i3}$ coincides with reordered projections $R_{i3}$. In other words, $S_{i3}$ is double sampled from $R_{i3}$, at the original locations and the middle points. Because these double sampled projections will be interpolated during the second stage backprojection, the added middle points have no effect on the reconstructed image. There is no difference in the result whether $R_{i3}$ or $S_{i3}$ is used for the backprojection, if the linear interpolation method is used in both the double sampling and the backprojection. The same applies to the double-sampled $S_{i1}$ and $S_{i5}$. For column 2, the double sampled $S_{i2}$ is a better representation of the original $R_{i2}$ than the single sampled $S_{i2}$. Thus, the double sampled $S_{i2}$ has less filtering effect than that of the single sampled $S_{i2}$, but not as good as the original $R_{i2}$, as does column 4. If 4M rows of interpolated $S_{ij}$ are interpolated, the quadruple-sampled $S_{i2}$ and $S_{i4}$ will have the same resolution as $R_{i2}$ and $R_{i4}$ in this example.

In this example, the locations of the interpolated projections $S_{ij}$ are increased by one row in every four channels with respect to the reordered projections $R_{ij}$. The fourfold interpolations will completely remove the degradation of image resolution. Beyond that, further increase in the number of interpolations will not enhance the resolution. It should be noted that doubling the number of interpolations will double the computations for the first stage of backprojection, but will not affect the amount of computations in the second stage.

In the actual detector geometry under a typical helical scan, even fourfold interpolation will not interpolate every column directly on the $R_{ij}$ locations. Yet it is impractical to have too many interpolations as they are costly in processing time. Therefore, in addition to the double, fourfold, or n-fold interpolation improvement, it is preferable to use a higher-order interpolation to further reduce the filtering effect.

Figure 24A:
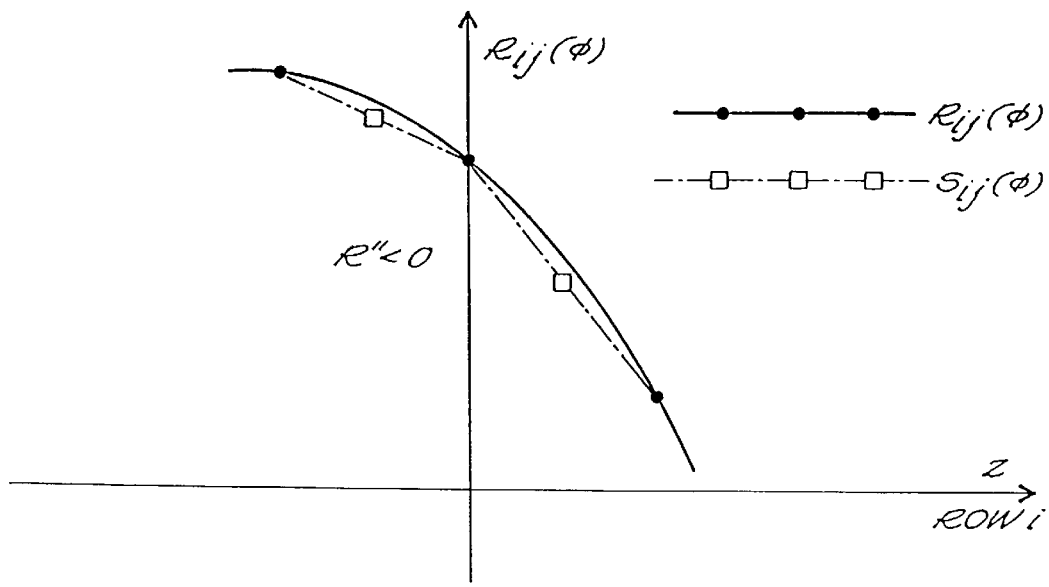
FIG. 24A is a chart of the variance of projection amplitude with respect to location along the z-axis, or row number i, for reordered projections $R_{ij}$ and constant-z-interpolated projections $S_{ij}$, in accordance with present invention.

Another drawback of the constants interpolation procedure described above is that it can possibly cause a special kind ring of artifact, when the density of the object varies rapidly along the z direction. To understand this potential problem, consider the variation of projection amplitude with respect to the z location, or row number i. If the second derivative of the reordered projections $R_{ij}(\phi)$ with respect to z, denoted by R", is less than 0 as shown in FIG. 24A, then interpolated projection $S_{ij}(\phi)$ will have a value less than that of $R_{ij}(\phi)$, except when it coincides with $R_{ij}(\phi)$. For a row i, the reordered projection $R_{ij}(\phi)$ may change gradually across many columns but the interpolated projection $S_{ij}(\phi)$ may deviate from $R_{ij}(\phi)$ in a periodic pattern.

Figure 24B:
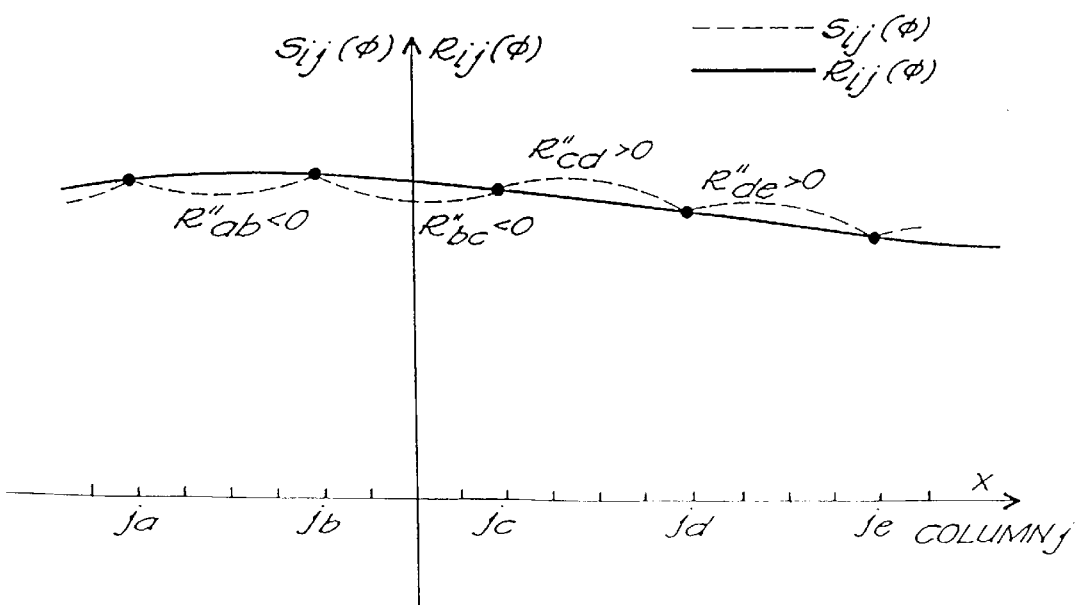
FIG. 24B is a chart of the variance of projection amplitude with respect to location along the x-axis, or column number j, for reordered projections $R_{ij}$ and constant-z-interpolated projections $S_{ij}$, in accordance with present invention.

Assume the second derivative R"<0 over the region between columns $j_a$ and $j_c$ and R">0 between $j_c$ and $j_e$, as shown in FIG. 24B. At column $j=j_a, j_b, j_c, j_d$, and $j_e$, the value of $S_{ij}(\phi)$ is equal to $R_{ij}(\phi)$, because the interpolating z position coincides with the original projection position. However, between these columns, the values of $S_{ij}(\phi)$ are either consistently less or greater than $R_{ij}(\phi)$. Consequently, the interpolated projection $S_{ij}(\phi)$ has pronounced values at column $j_a$ and $j_b$ greater than neighboring columns. The value of $S_{ij}(\phi)$ at column $j_c$ is less pronounced in this example, but it has pronounced values at column $j_d$ and $j_e$ smaller than the neighboring columns. Consequently, these few columns with pronounced values of $S_{ij}(\phi)$ tend to introduce a ring artifact on reconstructing slice in xy plane near the region where the object has rapid density change along the z direction but slow change on the xy plane.

There is another reason for the ring artifact to develop. In the constant-z interpolation procedure described above, those columns with interpolated z position coinciding with the original projection position, such as $j_a, j_b, j_c, j_d, j_e$ in FIG. 24B, remain the same columns for many view angles. During the backprojection process, the projection value of a column is backprojected along a path at a constant distance from the rotation center for all view angles. That is, the projection value of each column or each detector, is back-projected along the tangents of a circle. When this projection has a more pronounced value than the adjacent projections, a ring with pronounced image intensity appears on this circle. This situation is similar to the well-known problem of ring artifact in the conventional scanner, due to non-uniform gain in the detector array such that some detectors have more distinct projection values than adjacent detectors.

One way to disrupt the formation of the ring artifact is to shift gradually the location, or the column number, of these coincident columns, such as $j_a, j_b, j_c, j_d, j_e$ in FIG. 24B, to a nearby column in the successive view angles. This can be accomplished by including a view-angle dependent offset in the z position for interpolation. Instead of interpolation to a fixed z position for all view angles, $S_{ij}(\phi)$ is now interpolated to the constant-z position plus a small offset function offset $(\phi)$.

Using $z_{ij}(\phi)$ and $z_{ijo}(\phi)$ in Equations 16 and 17, the row number i' of the reordered $R_{i'j}(\phi)$ to be interpolated for $S_{ij}(\phi)$ can be determined by setting $$z_{i'j}(\phi)=z_{ijo}(\phi)+\text{offset}(\phi) \qquad (54)$$

from which, i' is obtained as in Equation 18

$$i'=i+(j-j_o)*\delta*D/(\Delta h*\pi)+\text{offset}(\phi) \qquad (55)$$

But unlike Equation 18, i' now depends on the view angle $\phi$. The function offset($\phi$) should vary slowly such that the interpolated projections maintain continuity over successive view angles. But it should also vary fast enough to prevent formation of the ring artifact. The peak-to-peak amplitude of offset($\phi$) is preferably equivalent to one row interval. In other words, in terms of the row unit, $$-0.5 \leq \text{offset}(\phi) \leq 0.5. \tag{56}$$

Figure 25:
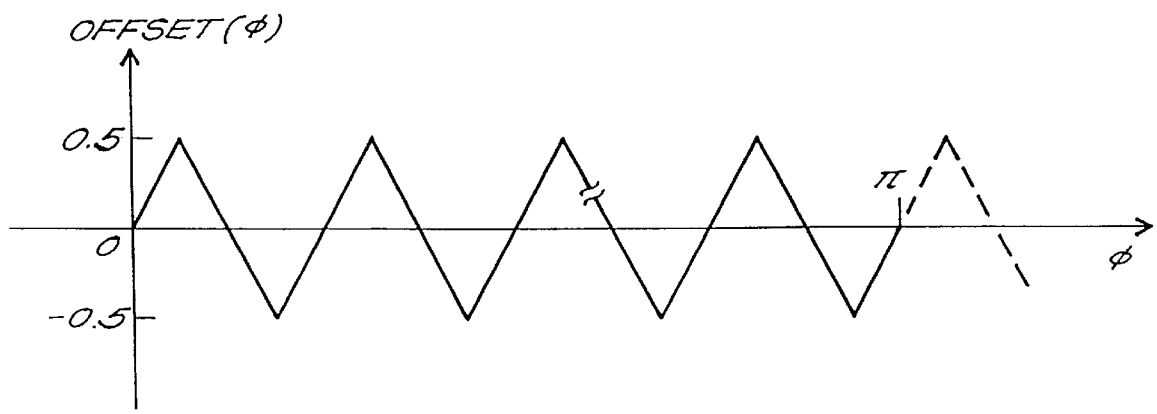
FIG. 25 illustrates a preferred periodic triangular offset function for resolving ring artifacts in accordance with the present invention.

The preferred shape of offset($\phi$) is a periodic triangular function as shown in FIG. 25 with about 10 periods over the $\phi$ range of 0 to $\pi$. The number of periods is chosen large enough to prevent formation of the ring artifact but also as small as possible to maintain continuity of the projection values in successive view angles.

The same offset($\phi$) function should be used in the backprojection. Instead of using the $z_1$ and $z_2$ from Equations 34, 35, and 48, the following equations are used:

$$z_1 = z' - z_a - \text{offset}(\phi)$$

$$z_2 = z' - z_b - \text{offset}(\phi) \tag{57}$$

in calculating for $i_z$ in Equations 39 and 41, or for $i_z[k]$ in Equations 50 and 52. The $i_z$ or $i_z[k]$ is then used for the second-stage interpolation in Equations 40 and 42 or in Equations 51 and 53. Notice z'=z, as given by Equation 31.

When twofold interpolation is used, the amplitude of the offset function offset($\phi$) of Equation 57, illustrated in FIG. 25, should be reduced by a factor or two, that is $$-0.25 \leq \text{offset}(\phi) \leq 0.25$$

Likewise, the amplitude of the offset function should be reduced by another factor of two if fourfold interpolation is used.

VIII. Conclusion

By reordering the transaxial fan beams into parallel projections in xy space and interpolating them to constant-z-positions, the reconstruction method of the present invention produces volumetric images superior to existing methods. Like the existing methods, the present invention is an approximation for helical cone-beam reconstruction, but is a better approximation than that of the prior art. In addition, reordering into parallel beams also simplifies the backprojection and reduces the number of computations and therefore allows for faster reconstruction.

Although in the description above, the constants interpolation precedes the interpolation for equal spatial intervals, this order of operation can be reversed. Alternatively, the interpolation for equal spatial intervals may be performed on the fan-beam projections $P_{ij}(\theta)$, before they are reordered into parallel-beam projections $R_{ij}(\phi)$.

In the first-stage backprojection, it is not necessary to interpolate for all rows of the projections $U_{ij}(\phi)$ and $U_{ij}(\phi+\pi)$. It is only necessary to interpolate for those rows of the projections which will be used in the second stage. From Equation 39, the minimum row number $iz_{min} \leq 1$ can be found for $U_{ij}(\phi)$. Similarly, from Equation 41 the maximum row number $iz_{max} \leq m$ can be found for $U_{ij}(\phi+\pi)$. It is preferred to interpolate only rows $iz_{min} \leq i < m$ for $U_{ij}(\phi)$ and $1 \leq i < iz_{max}$ for $U_{ij}(\phi+\pi)$.

For the vector processing algorithm, the minimum value of $iz_{min}$ and the maximum value of $iz_{max}$ among all channels $j_x[k]$ ranging from $j_x[1]$ through $j_x[n_x]$ will be used as the minimum row number of $U_{ij}(\phi)$ and maximum row number of $U_{ij}(\phi+\pi)$ respectively for the interpolation of the first stage of backprojection. It is preferable to pre-determine them based on those $iz_{min}$ and $iz_{max}$ calculated above and store into a lookup table. During the first stage of backprojection, these minimum and maximum row numbers will read in from the table to select only those rows of $U_{ij}(\phi)$ and $U_{ij}(\phi+\pi)$ within this range for the subsequent second stage of backprojection on $n_z$ arrays of voxels.

In the second-stage of backprojection, many computations are performed to find the addresses of the projections passing through each voxel. This can be expedited by using lookup tables, generally in the form of one-dimensional arrays. These tables can also be pre-interpolated to large sizes, such that the nearest neighbor approximation can be used to minimize the computing time.

Many computations in the backprojection are performed in preparation for the second-stage interpolation. They are shared by all xy-plane slices in the three-dimensional matrix. With more slices in one matrix, the overall computations will be more efficient. In other words, if the three-dimensional matrix is longer in the z-dimension, the overall image reconstruction will be faster.

While this invention has been particularly shown and described with references to preferred embodiments thereof, it will be understood by those skilled in the art that various changes in form and details may be made therein without departing from the spirit and scope of the invention as defined by the appended claims.

I claim:

1. A method of reconstructing a volumetric image of slices of an object in a computed tomography system including an energy source for projecting conical beams through the object toward a detector array of elements arranged in columns and in rows, each row arranged along a tangential direction centered about the source; said source and said detector array being in a predetermined spatial relationship and at least said source rotating about a rotation axis for interrogating the object at successive rotation angles as relative movement occurs substantially along the rotation axis between said object and said source and detector array; said method comprising:

at each rotation angle, sensing the beam intensity at each element of the detector array as projection data for the projection paths defined between each element and the source;

reordering the projection data of successive rotation angles into reordered projections, said reordered projections being parallel with respect to a plane perpendicular to the rotation axis and having different spatial positions along the rotation axis;

interpolating the reordered projections of adjacent rows to generate multiple rows of interpolated projections, each row of interpolated projections having a substantially common spatial position along the rotation axis; and backprojecting a plurality of slices, each from multiple rows of the interpolated projections so as to generate a volumetric image of said object therefrom.

2. The method of claim 1 wherein each of the rows lies on the perimeter of a circle centered at the source and in a plane substantially perpendicular to the rotation axis.

3. The method of claim 1 wherein the projection paths from each row of detectors comprise a transaxial fan, while the projection paths from each column of detectors comprise an axial fan.

4. The method of claim 3 wherein the reordered projections are reordered from projection data collected during a scan of the object comprising a half-scan in which the source and the detectors rotate over 180° plus the angular span of the transaxial fan such that the reordered projections have a view angle $\phi$ ranging from 0 to $\pi$ for reconstructing a section of the volumetric image along the rotation axis.

5. The method of claim 3 wherein the reordered projections are reordered from projection data collected during a scan of the object comprising a full-scan in which the source and the detectors rotate over 360° plus the angular span of the transaxial fan such that the reordered projections have a view angle φ ranging from 0 to 2π for reconstructing a section of the volumetric image data along the rotation axis.

6. The method of claim 1 wherein the step of interpolating comprises determining a midpoint of each projection path between the source and corresponding detector element to represent the spatial position of the projection path with respect to the rotation axis.

7. The method of claim 6 wherein the midpoints of projections of the same detector column lie along a line parallel to the rotation axis and wherein midpoints of projections of the same detector row lie on a circular arc centered at the source and intersecting the rotation axis.

8. The method of claim 6 wherein the midpoints of projections of the same detector column lie along a line parallel to the rotation axis and wherein midpoints of projections of the same detector row lie on a curve slightly deviated from a circular arc centered at the source and intersecting the rotation axis.

9. The method of claim 6 wherein the interpolated projections are interpolated from adjacent rows such that the interpolated projections have a substantially-constant spatial position along the rotation axis.

10. The method of claim 1 further comprising spatially-interpolating the projections of each row to provide equally-spaced projections having equal spatial intervals between adjacent columns.

11. The method of claim 1 further comprising filtering the interpolated projections with a convolution kernel.

12. The method of claim 1 further comprising calculating upper and lower separation lines for separating overlapping projections between view angles φ and φ+π and for defining the reordered projection of an axial fan therebetween for backprojection.

13. The method of claim 12 wherein the separation line is calculated as the line defined between respective positions of the source of the reordered projections at view angles φ and φ+π.

14. The method of claim 12 further comprising backprojecting those projections which lie within the separation lines of each axial fan, and discarding those projections beyond the separation lines.

15. The method of claim 1 wherein backprojecting comprises accumulating voxel data values from all projections passing through each voxel.

16. The method of claim 1 wherein backprojecting comprises backprojecting along the plane normal to the rotation axis as the most iterative computations, followed by backprojection along the rotation axis as the less iterative computations.

17. The method of claim 1 wherein interpolating comprises increasing the precision of interpolation by interpolating a larger number of projections at narrower spatial intervals to enhance image resolution.

18. The method of claim 1 wherein interpolating comprises using high-order spatial interpolation to increase the precision of interpolation.

19. The method of claim 1 further comprising applying a view-angle dependent offset function to the position of the reordered projections along the rotation axis.

20. The method of claim 19 wherein the offset function is a periodic triangular function.

21. The method of claim 1 wherein the incremental rotation angle Δθ is substantially equivalent to an incremental view angle Δφ, where Δφ is the angle between sets of reordered parallel projections.

22. The method of claim 21 wherein the incremental rotation angle Δθ is substantially equal to the angular spacing δ between columns, Δθ=δ; whereby the reordered projections are obtained by sorting the projection data without interpolation.

23. The method of claim 21 wherein the incremental rotation angle Δθ is not equal to the angular spacing δ between columns, Δθ≠δ; whereby the reordered projections are generated by interpolation of the projection data.

24. A computed tomography system for reconstructing a volumetric image of slices of an object including an energy source for projecting conical beams through the object toward a detector array of elements arranged in columns and in rows, each row arranged along a tangential direction centered about the source; said source and said detector array being in a predetermined spatial relationship and at least said source rotating about a rotation axis for interrogating the object at successive rotation angles as relative movement occurs substantially along the rotation axis between said object and said source detector array; said system comprising:

means for sensing at each rotation angle, the beam intensity at each element of the detector array as projection data for the projection paths defined between each element and the source;

means for reordering the projection data of successive rotation angles into reordered projections, said reordered projections being parallel with respect to a plane perpendicular to the rotation axis and having different spatial positions along the rotation axis;

means for interpolating the reordered projections of adjacent rows to generate multiple rows of interpolated projections, each row of interpolated projections having a substantially common spatial position along the rotation axis; and means for backprojecting a plurality of slices, each from multiple rows of the interpolated projections so as to generate a volumetric image of said object therefrom.

25. The computed tomography system of claim 24 wherein each of the rows lies on the perimeter of a circle centered at the source and in a plane substantially perpendicular to the rotation axis.

26. The computed tomography system of claim 24 wherein the projection paths from each row of detectors comprise a transaxial fan, while the projection paths from each column of detectors comprise an axial fan.

27. The computed tomography system of claim 26 wherein the reordered projections are reordered from projection data collected during a scan of the object comprising a half-scan in which the source and the detectors rotate over 180° plus the angular span of the transaxial fan such that the reordered projections have a view angle φ ranging from 0 to π for reconstructing a section of the volumetric image along the rotation axis.

28. The computed tomography system of claim 26 wherein the reordered projections are reordered from projection data collected during a scan of the object comprising a full-scan in which the source and the detectors rotate over 360° plus the angular span of the transaxial fan such that the reordered projections have a view angle φ ranging from 0 to 2π for reconstructing a section of the volumetric image data along the rotation axis.

29. The computed tomography system of claim 26 wherein the means for interpolating comprises determining a midpoint of each projection path between the source and corresponding detector element to represent the spatial position of the projection path with respect to the rotation axis.

30. The computed tomography system of claim 29 wherein the midpoints of projections of the same detector column lie along a line parallel to the rotation axis and wherein midpoints of projections of the same detector row lie on a circular arc centered at the source and intersecting the rotation axis.

31. The computed tomography system of claim 29 wherein the midpoints of projections of the same detector column lie along a line parallel to the rotation axis and wherein midpoints of projections of the same detector row lie on a curve slightly deviated from a circular arc centered at the source and intersecting the rotation axis.

32. The computed tomography system of claim 29 herein the interpolated projections are interpolated from adjacent rows such that the interpolated projections have a substantially-constant spatial position along the rotation axis.

33. The computed tomography system of claim 24 further comprising a spatial interpolator for spatially-interpolating the projections of each row to provide equally-spaced projections having equal spatial intervals between adjacent columns.

34. The computed tomography system of claim 24 further comprising a filter for filtering the interpolated projections with a convolution kernel.

35. The computed tomography system of claim 24 further comprising means for calculating upper and lower separation lines for separating overlapping projections between view angles $\phi$ and $\phi+\pi$ and for defining the reordered projection of an axial fan therebetween for backprojection.

36. The computed tomography system of claim 35 wherein the separation line is calculated as the line defined between respective positions of the source of the reordered projections at view angles $\phi$ and $\phi+\pi$.

37. The computed tomography system of claim 35 further comprising backprojecting those projections which lie within the separation lines of each axial fan, and discarding those projections beyond the separation lines.

38. The computed tomography system of claim 24 wherein the means for backprojecting comprises means for accumulating voxel data values from all projections passing through each voxel.

39. The computed tomography system of claim 24 wherein the means for backprojecting backprojects along the plane normal to the rotation axis as the most iterative computations, followed by backprojection along the rotation axis as the less iterative computations.

40. The computed tomography system of claim 24 wherein the means for interpolating increases the precision of interpolation by interpolating a larger number of projections at narrower spatial intervals to enhance image resolution.

41. The computed tomography system of claim 24 wherein the means for interpolating comprises using high-order spatial interpolation to increase the precision of interpolation.

42. The computed tomography system of claim 24 further comprising means for applying a view-angle dependent offset function to the position of the reordered projections along the rotation axis.

43. The computed tomography system of claim 42 wherein the offset function is a periodic triangular function.

44. The computed tomography system of claim 24 wherein the incremental rotation angle $\Delta\theta$ is substantially equivalent to an incremental view angle $\Delta\phi$, where $\Delta\phi$ is the angle between sets of reordered parallel projections.

45. The computed tomography system of claim 44 wherein the incremental rotation angle $\Delta\theta$ is substantially equal to the angular spacing $\delta$ between columns, $\Delta\theta=\delta$; whereby the reordered projections are obtained by sorting the projection data without interpolation.

46. The computed tomography system of claim 44 wherein the incremental rotation angle $\Delta\theta$ is not equal to the angular spacing $\delta$ between columns, $\Delta\theta\neq\delta$; whereby the reordered projections are generated by interpolation of the projection data.

47. A method for reconstructing a volumetric image of an object in a computed tomography system including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said method comprising:

at each rotation angle, sensing the beam intensity at each element of the detector array as projection data for the projection paths defined between each element and the source;

reordering the projection data of successive rotation angles into reordered projections, said reordered projections being parallel with respect to a plane perpendicular to the rotation axis and having different spatial positions along the rotation axis;

interpolating the reordered projections, by determining a midpoint of each projection path between the source and corresponding detector element to represent the spatial position of a projection path with respect to the rotation axis, wherein the midpoints of projections of the same detector column lie along a line parallel to the rotation axis and wherein midpoints of projections of the same detector row lie on a curve slightly deviated from a circular arc centered at the source and intersecting the rotation axis, to generate interpolated projections having a substantially common spatial position along the rotation axis; and backprojecting the interpolated projections to provide a volumetric image of said object.

48. A method for reconstructing a volumetric image of an object in a computed tomography system including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said method comprising:

at each rotation angle, sensing the beam intensity at each element of the detector array as projection data for the projection paths defined between each element and the source;

reordering the projection data of successive rotation angles into reordered projections, said reordered projections being parallel with respect to a plane perpendicular to the rotation axis and having different spatial positions along the rotation axis;

interpolating the reordered projections from adjacent rows, by determining a midpoint of each projection path between the source and corresponding detector element to represent the spatial position of a projection path with respect to the rotation axis, to generate interpolated projections having a substantially common spatial position along the rotation axis; and backprojecting the interpolated projections to provide a volumetric image of said object.

49. A method for reconstructing a volumetric image of an object in a computed tomography system including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said method comprising:

at each rotation angle, sensing the beam intensity at each element of the detector array as projection data for the projection paths defined between each element and the source;

reordering the projection data of successive rotation angles into reordered projections, said reordered projections being parallel with respect to a plane perpendicular to the rotation axis and having different spatial positions along the rotation axis;

interpolating the reordered projections to generate interpolated projections having a substantially common spatial position along the rotation axis;

calculating upper and lower separation lines for separating overlapping projections between view angles $\phi$ and $\phi+\pi$ and for defining the reordered projection of an axial fan therebetween; and backprojecting the interpolated projections to provide a volumetric image of said object.

50. The method of claim 49 wherein the separation line is calculated as the line defined between respective positions of the source of the reordered projections at view angles $\phi$ and $\phi+\pi$.

51. The method of claim 49 further comprising backprojecting those projections which lie within the separation lines of each axial fan, and discarding those projections beyond the separation lines.

52. A method for reconstructing a volumetric image of an object in a computed tomography system including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said method comprising:

at each rotation angle, sensing the beam intensity at each element of the detector array as projection data for the projection paths defined between each element and the source;

reordering the projection data of successive rotation angles into reordered projections, said reordered projections being parallel with respect to a plane perpendicular to the rotation axis and having different spatial positions along the rotation axis;

interpolating the reordered projections to generate interpolated projections having a substantially common spatial position along the rotation axis; and backprojecting the interpolated projections to provide a volumetric image of said object, wherein backprojecting comprises backprojecting along the plane normal to the rotation axis as the most iterative computations, followed by backprojection along the rotation axis as the less iterative computations.

53. A method for reconstructing a volumetric image of an object in a computed tomography system including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said method comprising:

at each rotation angle, sensing the beam intensity at each element of the detector array as projection data for the projection paths defined between each element and the source;

reordering the projection data of successive rotation angles into reordered projections, said reordered projections being parallel with respect to a plane perpendicular to the rotation axis and having different spatial positions along the rotation axis;

interpolating the reordered projections to generate interpolated projections having a substantially common spatial position along the rotation axis; and backprojecting the interpolated projections to provide a volumetric image of said object, wherein interpolating comprises increasing the precision of interpolation by interpolating a larger number of projections at narrower spatial intervals to enhance image resolution.

54. A method for reconstructing a volumetric image of an object in a computed tomography system including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said method comprising:

at each rotation angle, sensing the beam intensity at each element of the detector array as projection data for the projection paths defined between each element and the source;

reordering the projection data of successive rotation angles into reordered projections, said reordered projections being parallel with respect to a plane perpendicular to the rotation axis and having different spatial positions along the rotation axis;

interpolating the reordered projections to generate interpolated projections having a substantially common spatial position along the rotation axis; and backprojecting the interpolated projections to provide a volumetric image of said object, wherein interpolating comprises using high-order spatial interpolation to increase the precision of interpolation.

55. A method for reconstructing a volumetric image of an object in a computed tomography system including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said method comprising:

at each rotation angle, sensing the beam intensity at each element of the detector array as projection data for the projection paths defined between each element and the source;

reordering the projection data of successive rotation angles into reordered projections, said reordered projections being parallel with respect to a plane perpendicular to the rotation axis and having different spatial positions along the rotation axis;

applying a view-angle dependent offset function to the position of the reordered projections along the rotation axis;

interpolating the reordered projections to generate interpolated projections having a substantially common spatial position along the rotation axis; and backprojecting the interpolated projections to provide a volumetric image of said object.

56. The method of claim 55 wherein the offset function is a periodic triangular function.

57. A method for reconstructing a volumetric image of an object in a computed tomography system including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said method comprising:

at each rotation angle $\theta$, sensing the beam intensity at each element of the detector array as projection data for the projection paths defined between each element and the source;

reordering the projection data of successive rotation angles into reordered projections, each set of reordered projections having a view angle $\phi$, said reordered projections being parallel with respect to a plane perpendicular to the rotation axis and having different spatial positions along the rotation axis, wherein the incremental rotation angle $\Delta\theta$ is substantially equivalent to an incremental view angle $\Delta\phi$, where $\Delta\phi$ is the angle between sets of reordered parallel projections and wherein the incremental rotation angle $\Delta\theta$ is substantially equal to the angular spacing $\delta$ between columns, $\Delta\theta=\delta$;

interpolating the reordered projections to generate interpolated projections having a substantially common spatial position along the rotation axis; and backprojecting the interpolated projections to provide a volumetric image of said object.

58. A computed tomography system for reconstructing a volumetric image of an object including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said system comprising:

means for sensing at each rotation angle, the beam intensity at each element of the detector array as projection data for the projection paths defined between each element and the source;

means for reordering the projection data of successive rotation angles into reordered projections, said reordered projections being parallel with respect to a plane perpendicular to the rotation axis and having different spatial positions along the rotation axis;

means for interpolating the reordered projections by determining a midpoint of each projection path between the source and corresponding detector element to represent the spatial position of the projection path with respect to the rotation axis, wherein the midpoints of projections of the same detector column lie along a line parallel to the rotation axis and wherein midpoints of projections of the same detector row lie on a curve slightly deviated from a circular arc centered at the source and intersecting the rotation axis, to generate interpolated projections having a substantially common spatial position along the rotation axis; and means for backprojecting the interpolated projections to provide a volumetric image of said object.

59. A computed tomography system for reconstructing a volumetric image of an object including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said system comprising:

means for sensing at each rotation angle, the beam intensity at each element of the detector array as projection data for the projection paths defined between each element and the source;

means for reordering the projection data of successive rotation angles into reordered projections, said reordered projections being parallel with respect to a plane perpendicular to the rotation axis and having different spatial positions along the rotation axis;

means for interpolating the reordered projections from adjacent views by determining a midpoint of each projection path between the source and corresponding detector element to represent the spatial position of the projection path with respect to the rotation axis, to generate interpolated projections having a substantially common spatial position along the rotation axis; and means for backprojecting the interpolated projections to provide a volumetric image of said object.

60. A computed tomography system for reconstructing a volumetric image of an object including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said system comprising:

means for sensing at each rotation angle, the beam intensity at each element of the detector array as projection data for the projection paths defined between each element and the source;

means for reordering the projection data of successive rotation angles into reordered projections, said reordered projections being parallel with respect to a plane perpendicular to the rotation axis and having different spatial positions along the rotation axis;

means for interpolating the reordered projections to generate interpolated projections having a substantially common spatial position along the rotation axis;

means for calculating upper and lower separation lines for separating overlapping projections between view angles φ and φ+π and for defining the reordered projection of an axial fan therebetween; and means for backprojecting the interpolated projections to provide a volumetric image of said object.

61. The computed tomography system of claim 59 wherein the separation line is calculated as the line defined between respective positions of the source of the reordered projections at view angles φ and φ+π.

62. The computed tomography system of claim 59 further comprising backprojecting those projection which lie within the separation lines of each axial fan, and discarding those projections beyond the separation lines.

63. A computed tomography system for reconstructing a volumetric image of an object including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said system comprising:

means for sensing at each rotation angle, the beam intensity at each element of the detector array as projection data for the projection paths defined between each element and the source;

means for reordering the projection data of successive rotation angles into reordered projections, said reordered projections being parallel with respect to a plane perpendicular to the rotation axis and having different spatial positions along the rotation axis;

means for interpolating the reordered projections to generate interpolated projections having a substantially common spatial position along the rotation axis; and means for backprojecting the interpolated projections to provide a volumetric image of said object, wherein the means for backprojecting backprojects along the plane normal to the rotation axis as the most iterative computations, followed by backprojection along the rotation axis as the less iterative computations.

64. A computed tomography system for reconstructing a volumetric image of an object including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said system comprising:

means for sensing at each rotation angle, the beam intensity at each element of the detector array as projection data for the projection paths defined between each element and the source;

means for reordering the projection data of successive rotation angles into reordered projections, said reordered projections being parallel with respect to a plane perpendicular to the rotation axis and having different spatial positions along the rotation axis;

means for interpolating the reordered projections to generate interpolated projections having a substantially common spatial position along the rotation axis; and means for backprojecting the interpolated projections to provide a volumetric image of said object, wherein the means for interpolating increases the precision of interpolation by interpolating a larger number of projections at narrower spatial intervals to enhance image resolution.

65. A computed tomography system for reconstructing a volumetric image of an object including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said system comprising:

means for sensing at each rotation angle, the beam intensity at each element of the detector array as projection data for the projection paths defined between each element and the source;

means for reordering the projection data of successive rotation angles into reordered projections, said reordered projections being parallel with respect to a plane perpendicular to the rotation axis and having different spatial positions along the rotation axis;

means for interpolating the reordered projections to generate interpolated projections having a substantially common spatial position along the rotation axis; and means for backprojecting the interpolated projections to provide a volumetric image of said object, wherein the means for interpolating comprises using high-order spatial interpolation to increase the precision of interpolation.

66. A computed tomography system for reconstructing a volumetric image of an object including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said system comprising:

means for sensing at each rotation angle, the beam intensity at each element of the detector array as projection data for the projection paths defined between each element and the source;

means for reordering the projection data of successive rotation angles into reordered projections, said reordered projections being parallel with respect to a plane perpendicular to the rotation axis and having different spatial positions along the rotation axis;

means for applying a view-angle dependent offset function to the position of the reordered projections along the rotation axis;

means for interpolating the reordered projections to generate interpolated projections having a substantially common spatial position along the rotation axis; and means for backprojecting the interpolated projections to provide a volumetric image of said object.

67. The computed tomography system of claim 66 wherein the offset function is a periodic triangular function.

68. A computed tomography system for reconstructing a volumetric image of an object including an energy source for projecting conical beams through the object toward a detector array of elements arranged in columns along a rotation axis and in rows along a tangential direction centered about the source; said source and said detector array being in a predetermined spatial relationship and rotating about a rotation axis for interrogating the object at successive rotation angles as said object is translated substantially along the rotation axis; said system comprising:

means for sensing at each rotation angle, the beam intensity at each element of the detector array as projection data for the projection paths defined between each element and the source;

means for reordering the projection data of successive rotation angles into reordered projections, each set of reordered projections having a view angle $\phi$, said reordered projections being parallel with respect to a plane perpendicular to the rotation axis and having different spatial positions along the rotation axis, wherein the incremental rotation angle $\Delta\theta$ is substantially equivalent to an incremental view angle $\Delta\phi$, where $\Delta\phi$ is the angle between sets of reordered parallel projections, and wherein the incremental rotation angle $\Delta\theta$ is substantially equal to the angular spacing $\delta$ between columns, $\Delta\theta=\delta$;

means for interpolating the reordered projections to generate interpolated projections having a substantially common spatial position along the rotation axis; and means for backprojecting the interpolated projections to provide a volumetric image of said object.

\* \* \* \* \*

UNITED STATES PATENT AND TRADEMARK OFFICE
CERTIFICATE OF CORRECTION

PATENT NO.: 5,960,056

DATED: September 28, 1999

INVENTOR(S): Ching-Ming Lai

It is certified that errors appear in the above-identified patent and that said Letters Patent is hereby corrected as shown below:

Claim 32, column 25, line 13, delete "herein" and substitute therefor -- wherein --;

Claim 62, column 31, line 20, delete "projection" and substitute therefor -- projections --.

Signed and Sealed this

Thirtieth Day of May, 2000

Attest:

Q. TODD DICKINSON

Attesting Officer

Director of Patents and Trademarks